US011162079B2

(12) United States Patent
Schrepfer et al.

(10) Patent No.: US 11,162,079 B2
(45) Date of Patent: Nov. 2, 2021

(54) BLOOD TYPE O RH-HYPO-IMMUNOGENIC PLURIPOTENT CELLS

(71) Applicant: THE REGENTS OF THE UNIVERSITY OF CALIFORNIA, Oakland, CA (US)

(72) Inventors: Sonja Schrepfer, Burlingame, CA (US); Tobias Deuse, Burlingame, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/870,959

(22) Filed: May 9, 2020

(65) Prior Publication Data

US 2020/0354684 A1    Nov. 12, 2020

Related U.S. Application Data

(60) Provisional application No. 62/846,399, filed on May 10, 2019.

(51) Int. Cl.
| | |
|---|---|
| *A61K 9/127* | (2006.01) |
| *C12N 5/074* | (2010.01) |
| *C12N 5/0735* | (2010.01) |
| *C12N 5/077* | (2010.01) |

(52) U.S. Cl.
CPC ......... *C12N 5/0696* (2013.01); *C12N 5/0606* (2013.01); *C12N 5/0657* (2013.01); *C12N 2500/00* (2013.01); *C12N 2501/115* (2013.01); *C12N 2501/165* (2013.01); *C12N 2506/02* (2013.01); *C12N 2506/45* (2013.01); *C12N 2510/00* (2013.01)

(58) Field of Classification Search
CPC .............. A61K 9/0073; A61K 31/7088; A61K 48/0075; C12N 15/88
See application file for complete search history.

(56) References Cited

U.S. PATENT DOCUMENTS

| | | | |
|---|---|---|---|
| 4,427,777 A | 1/1984 | Goldstein | |
| 4,609,627 A | 9/1986 | Goldstein | |
| 5,606,042 A | 2/1997 | Smith et al. | |
| 5,633,130 A | 5/1997 | Smith et al. | |
| 5,731,426 A | 3/1998 | Smith et al. | |
| 6,184,017 B1 | 2/2001 | Smith et al. | |
| 7,413,904 B2 | 8/2008 | Gold et al. | |
| 8,796,443 B2 | 8/2014 | Khvorova et al. | |
| 10,047,340 B2 | 8/2018 | West | |
| 2004/0053836 A1 | 3/2004 | Mayer-Kuckuk et al. | |
| 2005/0048069 A1 | 3/2005 | Gorczynski et al. | |
| 2007/0274967 A1 | 11/2007 | Cao | |
| 2008/0095784 A1 | 4/2008 | Graziano et al. | |
| 2010/0135992 A1 | 6/2010 | Rother et al. | |
| 2012/0282174 A1 | 11/2012 | Weissman et al. | |
| 2019/0264177 A1 | 8/2019 | Kahvejian et al. | |
| 2019/0282618 A1 | 9/2019 | Rosen et al. | |

FOREIGN PATENT DOCUMENTS

| | | |
|---|---|---|
| GB | 2211504 A | 7/1989 |
| WO | WO9715664 A1 | 5/1997 |
| WO | WO9923210 A1 | 5/1999 |
| WO | 2003100018 A2 | 12/2003 |
| WO | 2004042346 A2 | 5/2004 |
| WO | WO2011146862 A1 | 11/2011 |
| WO | WO2013158292 A1 | 10/2013 |
| WO | WO201516740 A1 | 10/2015 |
| WO | 2016034679 A1 | 3/2016 |
| WO | WO2016073955 A2 | 5/2016 |
| WO | WO2016142532 A1 | 9/2016 |
| WO | WO2016183041 A2 | 11/2016 |
| WO | WO2017039445 A1 | 3/2017 |
| WO | WO2017064084 A1 | 4/2017 |
| WO | WO-2017/075276 A2 | 5/2017 |
| WO | WO2017079673 A1 | 5/2017 |

(Continued)

OTHER PUBLICATIONS

Focosi (Stem Cells Translational Medicine 2016;5:269-274).*

(Continued)

*Primary Examiner* — Valarie E Bertoglio
(74) *Attorney, Agent, or Firm* — Kaplan IP Law, P.C.; Jonathan M. Kaplan

(57) ABSTRACT

The invention discloses for the first time pluripotent cells, including hypoimmune pluripotent ABO blood type O Rhesus Factor negative (HIPO–) cells, that evade rejection by the host allogeneic immune system and avoid blood antigen type rejection. The HIPO– cells comprise reduced HLA-I and HLA-II expression, increased CD47 expression, and a universal blood group O Rh– ("O–") blood type. The universal blood type is achieved by eliminating ABO blood group A and B antigents as well as eliminating Rh factor expression, or by starting with an O– parent cell line. These new, novel HIPO– cells evade host immune rejection because they have an impaired antigen presentation capacity, protection from innate immune clearance, and lack blood group rejection. The cells of the invention also include O– pluripotent stem cells (iPSCO–) and O– embryonic stem cells (ESCO–). The invention further provides universally acceptable "off"-the-shelf pluripotent cells and derivatives thereof for generating or regenerating specific tissues and organs.

Figure 1A:
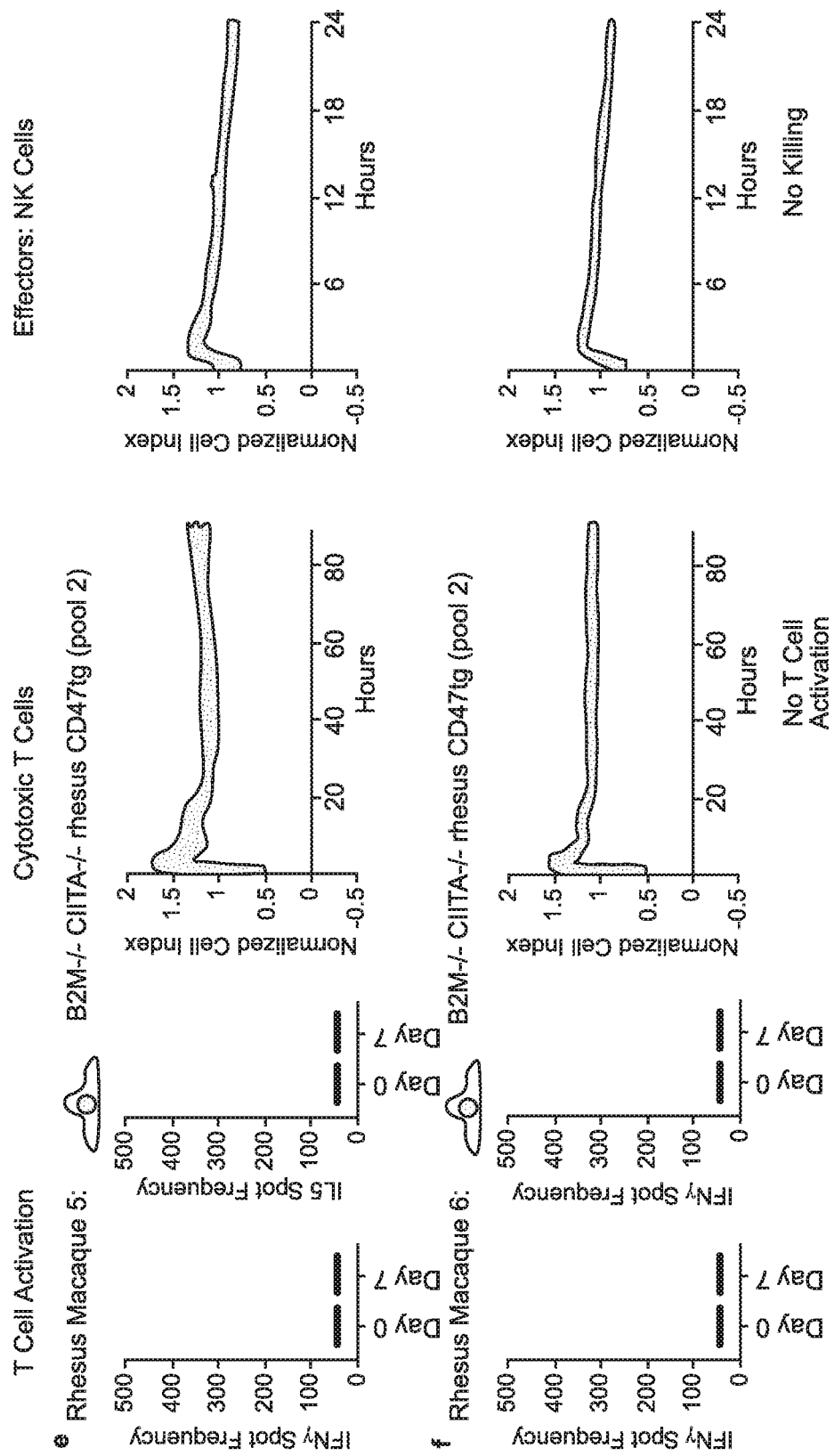

22 Claims, 5 Drawing Sheets
Specification includes a Sequence Listing.

(56) References Cited

FOREIGN PATENT DOCUMENTS

| WO | WO2018132783 A1 | 7/2018 |
|---|---|---|
| WO | 2018170046 A1 | 9/2018 |
| WO | WO2018227286 A2 | 12/2018 |
| WO | 2019045775 A1 | 3/2019 |
| WO | WO2020018615 A1 | 1/2020 |
| WO | WO2020018620 A1 | 1/2020 |

OTHER PUBLICATIONS

Seltsam (2003, Transfusion, 43:428-439).*
Han (May 2019, published online Apr. 30, 2019, PNAS, 116:10441-10446).*
Westhoff (HAABB, 52nd Annual Meeting, Apr. 9-10, 2019, Creating Customized Red Cell Reagents from iPSC Cells, accessed at http://www.haabb.org/images/06_HAA_Cultured_RBCS_as_reagents_Connie_Westhoff.pdf, accessed on Oct. 28, 2020).*
Li (BioScience, Aug. 2013 / vol. 63 No. 8, pp. 632-643).*
Lowry, 2008, PNAS, 105:2883-2888.*
Mallon (2014, Stem Cell Research, 12:376-386).*
Reijo et al. (2009, Differentiation, vol. 78, pp. 18-23).*
Reubinoff et al. (2000, Nature Biotechnology, vol. 18, pp. 399-404).*
Thomson, Science, 282: 1145-1147, 1998, at p. 1145, col. 2; p. 1145.*
Villartay, 1985, Tissue Antigens, 16:12-19.*
PCT Search Report and Written Opinion for PCT/US2018/013688, dated May 25, 2018.
Rong, Zhili et al. "An Effective Approach to Prevent Immune Rejection of Human ESC-Derived Allografts," Cell Stem Cell, vol. 14, No. 1, pp. 121-130, Jan. 2014.
Lu, Pengfei et al. "Generating Hypoimmunogenic Human Embryonic Stem Cells by the Disruption of Beta 2-Microglobulin," Stem Cell Reviews, vol. 9, No. 6, pp. 806-813, Aug. 2013.
Barclay, Neil et al. "The Interaction Between Signal Regulatory Protein Alpha and CD47: and Structure, Function, and Therapeutic Target," Annual Review of Immunology, vol. 32, No. 1, pp. 25-50, Mar. 2014.
PCT Search Report and Written Opinion for PCT/US2019/042123, dated Nov. 1, 2019.
Xiang, YR et al. "Eating" Cancer Cells by Blocking CD47 Signaling: Cancer Therapy by Targeting the Innate Immune Checkpoint, Cancer Transl Med, 3(6): 200-8 (2017).
Deuse, T et al. Hypoimmunogenic derivatives of induced pluripotent stem cells evade immune rejection in fully immunocompetent allogeneic recipients, Nature Biotechnology, vol. 37, No. 3, pp. 252-258 (2019).
PCT Search Report and Written Opinion for PCT/US2019/042117, dated Jan. 7, 2020.
Wang et al. Targeted Disruption of the B2-Microglobulin Gene Minimizes the Immunogenicity of Human Embryonic Stem Cells, Stem Cells Translational Medicine, 4:1234-1245 (2015).
Xu, Ling et al. The use of suicide gene systems in vascular cells in vitro, Cell Research 8, 73-78 (1998).
Lakshmipathy, Uma et al. Pluripotent Stem Cells Methods and Protocols, Spring Protocols, Humana Press (2013).
Barese, Cecilia N. et al. Thymidine Kinase Suicide Gene-mediated Ganciclovir Ablation of Autologous Gene-modified Rhesus Hematopoiesis, Molecular Therapy vol. 20. No. 10 (2012).
Wu, Chuanfeng et al. Development of an inducible caspase-9 safety switch for pluripotent stem cell-based therapies, Molecular Therapy—Methods & Clinical Development, 1, 14053 (2014).
Di Stasi, Antonio et al. Inducible Apoptosis as a Safety Switch for Adoptive Cell Therapy, The New England Journal of Medicine, 365:1673-83 (2011).
Tey, Siok-Keen et al. Inducible Caspase 9 Suicide Gene to Improve the Safety of Allodepleted T Cells after Haploidentical Stem Cell Transplantation, Biology of Blood and Marrow Transplantation, 13:913-924 (2007).

U.S. Appl. No. 62/698,941, filed Jul. 17, 2018.
U.S. Appl. No. 62/698,965, filed Jul. 17, 2018.
U.S. Appl. No. 62/698,973, filed Jul. 17, 2018.
U.S. Appl. No. 62/698,978, filed Jul. 17, 2018.
U.S. Appl. No. 62/698,981, filed Jul. 17, 2018.
U.S. Appl. No. 62/698,984, filed Jul. 17, 2018.
Abraches et al. Neural Differentiation of Embryonic Stem Cells In Vitro: A Road Map to Neurogenesis in the Embryo, PLoS ONE 4(7), 2009.
Adhikary, S. & Eilers, M., Transcriptional Regulation and Transformation by MYC Proteins, Nat. Rev. Mol. Cell Biol. 6:635-645, 2005.
Altschul et al., Basic Local Alignment Search Tool, J. Mol. Biol. 215:403-410, 1990.
Asgari et al., Differentiation and Transplantation of Human Induced Pluripotent Stem Cell-derived Hepatocyte-like Cells, Stem Cell Rev, DOI 10.1007/s12015-011-9330-y, 2011.
Burridge et al., A Universal System for Highly Efficient Cardiac Differentiation of Human Induced Pluripotent Stem Cells That Eliminates Interline Variability, PLoS One, 6(4):18293, 2011.
Chong et al. Human Embryonic Stem Cell-Derived Cardiomyocytes Regenerate Non-Human Primate Hearts, Nature 510(7504):273-7, 2014.
Cowan, C. A. et al. Derivation of Embryonic Stem-Cell Lines from Human Blastocysts, New England J. Med. 350:13, 2004.
Dang, D. T. et al. The biology of the mammalian Krüppel-like family of transcription factors, Int. J. Biochem. Cell Biol. 32:1103-1121, 2000.
Diecke et al. Novel codon-optimized mini-intronic plasmid for efficient, inexpensive, and xeno-free induction of pluripotency, Sci Rep. 5:8081, 2015.
Doudna and Charpentier. The new frontier of genome engineering with CRISPR-Cas9, Science 346, 2014.
Gornalusse et al. HLA-E-expressing pluripotent stem cells escape allogeneic responses and lysis by NK cells, Nature Biotech, 35(8):765-772, 2017.
Huangfu, et al. Induction of pluripotent stem cells by defined factors is greatly improved by small molecule compounds, Nature Biotechnol. 26 (7): 795, 2008.
Kamao et al. Characterization of Human Induced Pluripotent Stem Cell-Derived Retinal Pigment Epithelium Cell Sheets Aiming for Clinical Application, Stem Cell Reports 2:205-18, 2014.
Kattman et al. Stage-Specific Optimization of Activin/Nodal and BMP Signaling Promotes Cardiac Differentiation of Mouse and Human Pluripotent Stem Cell Lines, Cell Stem Cell 8:228-240, 2011.
Kawamura et al. Cardiomyocytes Derived from MHC-Homozygous Induced Pluripotent Stem Cells Exhibit Reduced Allogeneic Immunogenicity in MHC-Matched Non-human Primates, Stem Cell Reports 6(3): 312-320, 2016.
Kurmann et al. Regeneration of thyroid function by transplantation of differentiated pluripotent stem cells, 17(5): 527-542, 2015.
Liu et al. Efficient Differentiation ofMouse Embryonic Stem Cells into Insulin-Producing Cells, Exp. Diabetes Res, vol. 2012, Article ID 201295, 2012.
Liu et al., Human ESC-Derived Cardiomyocytes Restore Function in Infarcted Hearts of Non-Human Primates, Nat. Biotechnol. 36(7):597-605, 2018.
Loh et al. Mapping the pairwise choices leading from pluripotency to human bone, heart and other mesoderm cell-types, Cell, 166(2): 451-467, 2016.
Mandai et al. Autologous Induced Stem-Cell-Derived Retinal Cells for Macular Degeneration, New England Journal of Medicine, 376:1038-46, 2017.
Muraro et al. A Single-Cell Transcriptome Atlas of the Human Pancreas, Cell Systems 3, 385-394, 2016.
Needleman & Wunsch, A General Method Applicable to the Search for Similarities in the Amino Acid Sequence of Two Proteins, J. Mol. Biol. 48:443, 1970.
Pagliuca et al. Generation of Functional Human Pancreatic b Cells In Vitro, Cell 159, 428-439, 2014.
Pearson & Lipman, Improved tools for biological sequence comparison, Proc. Nat'l Acad. Sci. USA 85:2444, 1988.

(56) References Cited

OTHER PUBLICATIONS

Pettinato et al. Scalable Differentiation of Human iPSCs in a Multicellular Spheroid-based 3D Culture into Hepatocyte-like Cells through Direct Wnt/β-catenin Pathway Inhibition, Scientific Reports | 6:32888 | DOI: 10.1038/srep32888, 2016.
Prasain et al. Differentiation of human pluripotent stem cells to cells similar to cord-blood endothelial colony-forming cells, Nat Biotechnol. 32(11): 1151-1157, 2014.
Ryan et al. POU domain family values: flexibility,partnerships, and developmental codes, Genes Dev. 11:1207-1225, 1997.
Saljo et al. HLA and Histo-Blood Group Antigen Expression in Human Pluripotent Stem Cells and their Derivatives, Scientific Reports. 13072: 1-14, 2017.
Seki et al. Methods of induced pluripotent stem cells for clinical application, World J. Stem Cells 7(1):116-125, 2015.
Sharma et al. Derivation of Highly Purified Cardiomyocytes from Human Induced Pluripotent Stem Cells Using Small Molecule-modulated Differentiation and Subsequent, Glucose Starvation, J. Vis Exp. 2015.
Shiba et al. hESC-Derived Cardiomyocytes Electrically Couple and Suppress Arrhythmias in Injured Hearts, Nature 489(7415):322-5, 2012.
Si-Tayeb et al. Highly Efficient Generation of Human Hepatocyte-Like Cells from Induced Pluripotent Stem Cells, Hepatology 51:297-305, 2010.
Smith & Waterman. Comparison of Biosequences, Adv. Appl. Math. 2:482, 1981.
Takahashi et al. Induction of Pluripotent Stem Cells from Mouse Embryonic and Adult Fibroblast Cultures by Defined Factors, Cell 126:663-676, 2006.
Vegas et al. Long term Glycemic Control Using Polymer Encapsulated, Human Stem-Cell Derived β-cells in Immune Competent mice, Nat Med. 22(3): 306-311, 2016.
Woltjen et al. piggyBac transposition reprograms fibroblasts to induced pluripotent stem cells, Nature 458 (7239): 766-770, 2009.
Zhou et al. Adenoviral Gene Delivery Can Reprogram Human Fibroblasts to Induced Pluripotent Stem Cells, Stem Cells 27 (11): 2667-74, 2009.
Zhou et al. Generation of Induced Pluripotent Stem Cells Using Recombinant Proteins, Cell Stem Cell 8:381-384, 2009.
Ellis et al. Regenerative medicine and cell-based approaches to restore pancreatic function, Nature Reviews, vol. 14, 612-628, 2017.
Fiers et al., Complete nucleotide sequence of SV40 DNA, Nature 273: 113-120, 1978.
Greenaway P. J. et al. Human cytomegalovirus DNA: BamHI, EcoRI and Pst I restriction endonuclease cleavage maps, Gene 18: 355-360,1982.
Huang et al. Differentiation of human embryonic stem cells into smooth muscle cells in adherent monolayer culture, Biochem Biophys Res Commun 351(2)321-7, 2006.
Nakagawa et al. Generation of induced pluripotent stem cells without Myc from mouse and human fibroblasts, Nature Biotechnology 26:101-106, 2007.
Shiba et al. Allogeneic transplantation of iPS cell-derived cardiomyocytes regenerates primate hearts, Nature 538 (7625):388-391, 2016.
Snykers et al., Hepatic Differentiation of Mesenchymal Stem Cells: In Vitro Strategies, Methods Mol Biol 698:305-314, 2011.
Olsson et al. Universal red blood cells—enzymatic conversion of blood group A and B antigens, Transfusion Clinique et Biologique 11: 33-39, 2004.

Mölne et al. Embryonic Stem Cells and in Differentiated Hepatocyte- and Cardiomyocyte-Like Cells, Transplantation, 86(10):1407-13 (2008).
PCT Search Report and Written Opinion dated Mar. 17, 2021 issued in PCT Application No. PCT/US2020/055120.
Apostolou et al., "iPS cells under attack" Nature, vol. 474, pp. 165-166 (2011).
Food and Drug Administration, Guidance for Industry, Eligibility Determination for Donors of Human Cells, Tissues, and Cellular and Tissue-Based Products (HCT/Ps), Aug. 2007.
IPSC transplantation clinical trials; World Wide Web at clinicaltrials.gov/ct2/results?cond=transplantation&term=iPSC&cntry=&state=&city=&dist=.
Shiina, T et al., "The HLA genomic loci map: expression, interaction, diversity and disease" Journal of Human Genetics, 54:15-39 (2009).
Berry, B. et al., "Advances and Current Challenges Associated with the Use of Human Induced Pluripotent Stem Cells in Modeling . . . " Cells Tissues Organs 2018; 205:331-349.
Clarke et al. "Ensuring source material consistency and continuity for commercialization of advanced therapies," Cell & Gene Therapy Insights 2020; 6(2), 295-305.
Maruyama, Y. "Session I Considerations for Screening/Transferring Cells for Further Manufacturing," Pharmaceuticals and Medical Devices Agency (2016).
Tsuji et al., "Concise Review: Laying the Groundwork for a First-In-Human Study of an Induced Pluripotent Stem Cell-Based . . . " Stem Cells, 37:6-13 (2019).
Hawksworth et al., "Enhancement of red blood cell transfusion compatibility using CRISPR-mediated erythroblast gene editing," EMBO Mol Med, vol. 10, No. 6, Apr. 26, 2018.
PCT Search Report and Written Opinion for PCT/US2020/032272, dated Oct. 30, 2020.
PCT Search Report and Written Opinion for PCT/US2020/039220, dated Oct. 30, 2020.
Murata, Y et al. "Anti-human SIRPa antibody is a new tool for cancer immunotherapy," Cancer Science, vol. 109, pp. 1300-1308, 2018.
Nath, PR, CD47 Expression in natural killer cells regulates homeostasis and modulates immune response to lymphocytic choriomeningitis virus, Front Immunol vol. 9, 2018.
Pan, YF, Signal Regulatory Protein a is associated with tumor-polarized macrophages phenotype switch and plays a pivotal role in tumor progression.Hepatology,vol. 58 No. 2, 2013.
Breimer et al. Glycosphingolipids of human embryonic stem cells, Glycoconj J (2017) 34:713-723, Published online 2016.
Lee et al. Evaluation of 28 Human Embryonic Stem Cell Lines for Use as Unrelated Donors in Stem Cell Therapy: Implications of HLA and ABO Genotypes, Cell Transplantation, vol. 19, pp. 1383-1395, 2010.
Romagnuolo et al. Human Embryonic Stem Cell-Derived Cardiomyocytes Regenerate the Infarcted Pig Heart but Induce Ventricular Tachyarrhythmias, Stem Cell Reports (2019), https://doi.org/10.1016/j.stemcr.2019.04.005.
Taylor et al. Immunological considerations for embryonic and induced pluripotent stem cell banking, Phil. Trans. R. Soc. B (2011) 366, 2312-2322.
PCT Search Report and Written Opinion dated Jul. 22, 2021 issued in PCT Application No. PCT/US2021/013499.

\* cited by examiner

SEQUENCE LISTING

<160> NUMBER OF SEQ ID NOS: 13

<210> SEQ ID NO 1
<211> LENGTH: 119
<212> TYPE: PRT
<213> ORGANISM: Homo sapiens

<400> SEQUENCE: 1

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Ile
        115

<210> SEQ ID NO 2
<211> LENGTH: 160
<212> TYPE: PRT
<213> ORGANISM: Homo sapiens

<400> SEQUENCE: 2

Met Arg Cys Leu Ala Pro Arg Pro Ala Gly Ser Tyr Leu Ser Glu Pro
1               5                   10                  15

Gln Gly Ser Ser Gln Cys Ala Thr Met Glu Leu Gly Pro Leu Glu Gly
            20                  25                  30

Gly Tyr Leu Glu Leu Leu Asn Ser Asp Ala Asp Pro Leu Cys Leu Tyr
        35                  40                  45

His Phe Tyr Asp Gln Met Asp Leu Ala Gly Glu Glu Ile Glu Leu
    50                  55                  60

Tyr Ser Glu Pro Asp Thr Asp Thr Ile Asn Cys Asp Gln Phe Ser Arg
65                  70                  75                  80

Leu Leu Cys Asp Met Glu Gly Asp Glu Glu Thr Arg Glu Ala Tyr Ala
                85                  90                  95

Asn Ile Ala Glu Leu Asp Gln Tyr Val Phe Gln Asp Ser Gln Leu Glu
            100                 105                 110

Gly Leu Ser Lys Asp Ile Phe Lys His Ile Gly Pro Asp Glu Val Ile
        115                 120                 125

Gly Glu Ser Met Glu Met Pro Ala Glu Val Gly Gln Lys Ser Gln Lys
    130                 135                 140

Arg Pro Phe Pro Glu Glu Leu Pro Ala Asp Leu Lys His Trp Lys Pro
145                 150                 155                 160

<210> SEQ ID NO 3
<211> LENGTH: 293
<212> TYPE: PRT
<213> ORGANISM: Homo sapiens

<400> SEQUENCE: 3

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Glu
    290

<210> SEQ ID NO 4
<211> LENGTH: 376
<212> TYPE: PRT
<213> ORGANISM: Herpes simplex virus type 1

<400> SEQUENCE: 4

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
```

```
                65                  70                  75                  80
        Val Pro Glu Pro Met Thr Tyr Trp Gln Val Leu Gly Ala Ser Glu Thr
                        85                  90                  95

Ile Ala Asn Ile Tyr Thr Thr Gln His Arg Leu Asp Gln Gly Glu Ile
                        100                 105                 110

Ser Ala Gly Asp Ala Ala Val Val Met Thr Ser Ala Gln Ile Thr Met
                        115                 120                 125

Gly Met Pro Tyr Ala Val Thr Asp Ala Val Leu Ala Pro His Val Gly
                130                 135                 140

Gly Glu Ala Gly Ser Ser His Ala Pro Pro Ala Leu Thr Leu Ile
        145                 150                 155                 160

Phe Asp Arg His Pro Ile Ala Ala Leu Leu Cys Tyr Pro Ala Ala Arg
                        165                 170                 175

Tyr Leu Met Gly Ser Met Thr Pro Gln Ala Val Leu Ala Phe Val Ala
                        180                 185                 190

Leu Ile Pro Pro Thr Leu Pro Gly Thr Asn Ile Val Leu Gly Ala Leu
                        195                 200                 205

Pro Glu Asp Arg His Ile Asp Arg Leu Ala Lys Arg Gln Arg Pro Gly
                        210                 215                 220

Glu Arg Leu Asp Leu Ala Met Leu Ala Ala Ile Arg Arg Val Tyr Gly
        225                 230                 235                 240

Leu Leu Ala Asn Thr Val Arg Tyr Leu Gln Gly Gly Ser Trp Trp
                        245                 250                 255

Glu Asp Trp Gly Gln Leu Ser Gly Thr Ala Val Pro Pro Gln Gly Ala
                        260                 265                 270

Glu Pro Gln Ser Asn Ala Gly Pro Arg Pro His Ile Gly Asp Thr Leu
                        275                 280                 285

Phe Thr Leu Phe Arg Ala Pro Glu Leu Leu Ala Pro Asn Gly Asp Leu
                        290                 295                 300

Tyr Asn Val Phe Ala Trp Ala Leu Asp Val Leu Ala Lys Arg Leu Arg
        305                 310                 315                 320

Pro Met His Val Phe Ile Leu Asp Tyr Asp Gln Ser Pro Ala Gly Cys
                        325                 330                 335

Arg Asp Ala Leu Leu Gln Leu Thr Ser Gly Met Val Gln Thr His Val
                        340                 345                 350

Thr Thr Pro Gly Ser Ile Pro Thr Ile Cys Asp Leu Ala Arg Thr Phe
                        355                 360                 365

Ala Arg Glu Met Gly Glu Ala Asn
                        370                 375

<210> SEQ ID NO 5
<211> LENGTH: 427
<212> TYPE: PRT
<213> ORGANISM: Escherichia coli

<400> SEQUENCE: 5

Met Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
                20                  25                  30

Ile Asp Ala Gln Ser Gly Val Met Pro Ile Thr Glu Asn Ser Leu Asp
                35                  40                  45

Ala Glu Gln Gly Leu Val Ile Pro Pro Phe Val Glu Pro His Ile His
        50                  55                  60
```

-continued

```
Leu Asp Thr Thr Gln Thr Ala Gly Gln Pro Asn Trp Asn Gln Ser Gly
 65                  70                  75                  80

Thr Leu Phe Glu Gly Ile Glu Arg Trp Ala Glu Arg Lys Ala Leu Leu
                 85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
            115                 120                 125

Ala Thr Leu Thr Ala Leu Lys Ala Met Leu Glu Val Lys Gln Glu Val
    130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
                165                 170                 175

Gly Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
            195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
            275                 280                 285

Thr Tyr Pro Lys Arg Arg Gly Ile Thr Arg Val Lys Glu Met Leu Glu
    290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
            355                 360                 365

Ile Ala Ala Gly Asn Ser Ala Asn Leu Ile Ile Leu Pro Ala Glu Asn
    370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg
            420                 425

<210> SEQ ID NO 6
<211> LENGTH: 282
<212> TYPE: PRT
<213> ORGANISM: Homo sapiens

<400> SEQUENCE: 6

Gly Phe Gly Asp Val Gly Ala Leu Glu Ser Leu Arg Gly Asn Ala Asp
1               5                   10                  15
```

```
Leu Ala Tyr Ile Leu Ser Met Glu Pro Cys Gly His Cys Leu Ile Ile
             20                  25                  30

Asn Asn Val Asn Phe Cys Arg Glu Ser Gly Leu Arg Thr Arg Thr Gly
         35                  40                  45

Ser Asn Ile Asp Cys Glu Lys Leu Arg Arg Phe Ser Ser Leu His
 50                  55                  60

Phe Met Val Glu Val Lys Gly Asp Leu Thr Ala Lys Lys Met Val Leu
 65                  70                  75                  80

Ala Leu Leu Glu Leu Ala Gln Gln Asp His Gly Ala Leu Asp Cys Cys
                 85                  90                  95

Val Val Val Ile Leu Ser His Gly Cys Gln Ala Ser His Leu Gln Phe
                100                 105                 110

Pro Gly Ala Val Tyr Gly Thr Asp Gly Cys Pro Val Ser Val Glu Lys
             115                 120                 125

Ile Val Asn Ile Phe Asn Gly Thr Ser Cys Pro Ser Leu Gly Gly Lys
130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
            195                 200                 205

Val Ser Tyr Ser Thr Phe Pro Gly Phe Val Ser Trp Arg Asp Pro Lys
            210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
            275                 280

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgtgagtaaa cctgaatctt                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatattggca taagcctccc                                                20
```

```
<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tggggccaaa tcatgtagac tc                                                  22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcagtggggg tgaattcagt gt                                                  22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cttaacagcg atgctgaccc c                                                   21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggcctccat ctcccctctc tt                                                  22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccagtggggc actattgtac                                                     20
```

BLOOD TYPE O RH-HYPO-IMMUNOGENIC PLURIPOTENT CELLS

I. CROSS REFERENCE TO RELATED APPLICATIONS

This application claims the benefit of U.S. Provisional application No. 62/846,399, filed on May 10, 2019, which is incorporated herein by reference in its entirety.

This invention was made with government support under grant no. RO1 HL140236 awarded by The National Institutes of Health. The government has certain rights in the invention.

I.I SEQUENCE LISTING

The instant application contains a Sequence Listing which has been submitted electronically in ASCII format and is hereby incorporated by reference in its entirety. Said ASCII copy, created on Jun. 17, 2020, is named RUC012US1_SL.txt and is 16,405 bytes in size.

II. FIELD OF THE INVENTION

Regenerative cell therapy is an important potential treatment for regenerating injured organs and tissue. With the low availability of organs for transplantation and the accompanying lengthy wait, the possibility of regenerating tissue by transplanting readily available cell lines into patients is understandably appealing. Regenerative cell therapy has shown promising initial results for rehabilitating damaged tissues after transplantation in animal models (e.g. after myocardial infarction). The propensity for the transplant recipient's immune system to reject allogeneic material, however, greatly reduces the potential efficacy of therapeutics and diminishes the possible positive effects surrounding such treatments.

III. BACKGROUND OF THE INVENTION

Regenerative cell therapy is an important potential treatment for regenerating injured organs and tissue. With the low availability of organs for transplantation and the accompanying lengthy wait, the possibility of regenerating tissue by transplanting readily available cell lines into patients is understandably appealing. Regenerative cell therapy has shown promising initial results for rehabilitating damaged tissues after transplantation in animal models (e.g. after myocardial infarction). The propensity for the transplant recipient's immune system to reject allogeneic material, however, greatly reduces the potential efficacy of therapeutics and diminishes the possible positive effects surrounding such treatments.

Autologous induced pluripotent stem cells (iPSCs) theoretically constitute an unlimited cell source for patient-specific cell-based organ repair strategies. Their generation, however, poses technical and manufacturing challenges and is a lengthy process that conceptually prevents any acute treatment modalities. Allogeneic iPSC-based therapies or embryonic stem cell-based therapies are easier from a manufacturing standpoint and allow the generation of well-screened, standardized, high-quality cell products. Because of their allogeneic origin, however, such cell products would undergo rejection. With the reduction or elimination of the cells' antigenicity, universally-acceptable cell products could be produced. Because pluripotent stem cells can be differentiated into any cell type of the three germ layers, the potential application of stem cell therapy is wide-ranging. Differentiation can be performed ex vivo or in vivo by transplanting progenitor cells that continue to differentiate and mature in the organ environment of the implantation site. E vivo differentiation allows researchers or clinicians to closely monitor the procedure and ensures that the proper population of cells is generated prior to transplantation.

In most cases, however, undifferentiated pluripotent stem cells are avoided in clinical transplant therapies due to their propensity to form teratomas. Rather, such therapies tend to use differentiated cells (e.g. stem cell-derived cardiomyocytes transplanted into the myocardium of patients suffering from heart failure). Clinical applications of such pluripotent cells or tissues would benefit from a "safety feature" that controls the growth and survival of cells after their transplantation.

The art seeks stem cells capable of producing cells that are used to regenerate or replace diseased or deficient cells. Pluripotent stem cells (PSCs) may be used because they rapidly propagate and differentiate into many possible cell types. The family of PSCs includes several members generated via different techniques and possessing distinct immunogenic features. Patient compatibility with engineered cells or tissues derived from PSCs determines the risk of immune rejection and the requirement for immunosuppression.

Embryonic stem cells (ESCs) isolated from the inner cell mass of blastocysts exhibit the histocompatibility antigens that are mismatches with recipients. This immunological barrier cannot be solved by human leukocyte antigen (HLA)-typed banks of ESCs because even HLA-matched PSC grafts undergo rejection because of mismatches in non-HLA molecules that function as minor antigens. This is also true for allogeneic induced pluripotent stem cells (iPSCs).

To circumvent the problem of rejection, different techniques for the generation of patient-specific pluripotent stem cells have been developed. These include the transfer of a somatic cell nucleus into an enucleated oocyte (somatic cell nucleus transfer (SCNT) stem cells), the fusion of a somatic cell with an ESC (hybrid cell), and the reprogramming of somatic cells using certain transcription factors (induced PSCs or iPSCs). SCNT stem cells and iPSCs, however, may have immune incompatibilities with the nucleus or cell donor, respectively, despite chromosomal identity. SCNT stem cells carry mitochondrial DNA (mtDNA) passed along from the oocyte. mtDNA-coded proteins can act as relevant minor antigens and trigger rejection. DNA and mtDNA mutations and genetic instability associated with reprogramming and culture-expansion of iPSCs can also create minor antigens relevant for immune rejection. This hurdle decreases the likelihood of successful, large-scale engineering of compatible patient-specific tissues using SCNT stem cells or iPSCs.

Blood is classified into different groups according to the presence or absence of antigens on the surface of every red blood cell in a person's body (ABO Blood Type). The A, B, AB, and A1 antigens are determined by the sequence of oligosaccharides on the glycoproteins of erythrocytes. The genes in the blood group antigen group provide instructions for making antigen proteins. Blood group antigen proteins serve a variety of functions within the cell membrane of red blood cells. These protein functions include transporting other proteins and molecules into and out of the cell, maintaining cell structure, attaching to other cells and molecules, and participating in chemical reactions.

The Rhesus Factor (Rh) blood group is the second most important blood group system, after the ABO blood group system. The Rh blood group system consists of 49 defined blood group antigens, among which the five antigens D, C, c, E, and e are the most important. There is no d ("little d") antigen. Rh(D) status of an individual is normally described with a positive or negative suffix after the ABO type. The terms Rh factor, Rh positive, and Rh negative refer to the Rh(D) antigen only. Antibodies to Rh antigens can be involved in hemolytic transfusion reactions and antibodies to the Rh(D) and Rh(c) antigens confer significant risk of hemolytic disease of the fetus and newborn. ABO antibodies develop in early life in every human. However, rhesus antibodies in Rh– humans develop only when the person is sensitized. This occurs by giving birth to a rh+ baby or by receiving an Rh+ blood transfusion.

Transfusion of an ABO or Rh-incompatible red blood cell unit can lead to potentially fatal complications caused by sudden massive immune haemolysis of the transfused RBC, haemoglobinuria and disseminated intravascular coagulation. To date, cell transplantation technologies have not taken ABO blood types into account. See. e.g., Chong et al., *Nature* 510(7504):273-7 (2014); Liu et al., *Nat. Biotechnol.* 36(7):597-605 (2018); Shiba et al., *Nature* 489(7415):322-5 (2012); Shiba et al., *Nature* 38(7625):388-391 (2016); Kawamura et al., *Stem Cell Reports* 6(3): 312-320 (2016).

IV. SUMMARY OF THE INVENTION

The invention discloses for the first time pluripotent cells, including hypoimmune pluripotent ABO blood type O Rhesus Factor negative (HIPO–) cells, that evade rejection by the host allogeneic immune system and avoid blood antigen type rejection. The HIPO– cells comprise reduced HLA-I and HLA-II expression, increased CD47 expression, and a universal blood group O Rh– ("O–") blood type. The universal blood type is achieved by eliminating ABO blood group A and B antigens as well as eliminating Rh factor expression, or by starting with an O– parent cell line. These new, novel HIPO– cells evade host immune rejection because they have an impaired antigen presentation capacity, protection from innate immune clearance, and lack blood group rejection. The cells of the invention also include O– pluripotent stem cells (iPSCO–) and O– embryonic stem cells (ESCO–). The invention further provides universally acceptable "off"-the-shelf pluripotent cells and derivatives thereof for generating or regenerating specific tissues and organs.

Thus, the invention provides a human hypo-immunogenic pluripotent cell comprising: an endogenous Major Histocompatibility Antigen Class I (HLA-I) function that is reduced when compared to a parent pluripotent cell; an endogenous Major Histocompatibility Antigen Class II (HLA-II) function that is reduced when compared to the parent pluripotent cell; an increased CD47 function that reduces susceptibility to NK cell killing; an ABO blood group type O (O); and a Rhesus Factor (Rh) blood type negative (–); wherein the human hypo-immunogenic pluripotent O– (HIPO–) cell is less susceptible to rejection when transplanted into a subject when compared with an otherwise similar hypo-immunogenic pluripotent (HIP) cell that is an ABO blood group or Rh factor mismatch to the subject.

In some aspects of the invention, the HIPO– cell is selected from the group consisting of a human, cow, pig, chicken, turkey, horse, sheep, goat, donkey, mule, duck, goose, buffalo, camel, yak, llama, alpaca, mouse, rat, dog, cat, hamster, and guinea pig. In other aspects, the ABO blood group type O results from a reduced ABO blood group protein expression. In other aspects, the ABO blood group is endogenously type O.

In some aspects of the invention, the HIPO– cell has an ABO blood group type O that results from a disruption in human Exon 7 of the ABO gene. In other aspects, the ABO blood group type O results from an enzymatic modification of an ABO gene product on a surface of the HIPO– cell. In a preferred aspect, the enzymatic modification removes a carbohydrate from the ABO gene product. In another preferred aspect, the enzymatic modification removes a carbohydrate from an ABO A1 antigen, A2 antigen, or B antigen.

In an aspect of the invention, the HIPO– cell Rh blood group is endogenously type Rh–. In another aspect, the Rh blood group results from a reduced Rh protein expression. In another aspect, the type Rh– results from a disruption in an Rh C antigen, an Rh E antigen, a Kell K antigen (KEL), a Duffy (FY) Fya antigen, a Duffy Fy3 antigen, a Kidd (JK) Jkb antigen, or a Kidd SLC14A1 gene.

In an aspect of the invention, the HIPO– cell has a reduced HLA-I function by virtue of a reduction in ß-2 microglobulin protein expression. In another aspect, a gene encoding the ß-2 microglobulin protein is knocked out. In a preferred aspect, the ß-2 microglobulin protein has at least a 90% sequence identity to SEQ ID NO:1. In a more preferred aspect, the ß-2 microglobulin protein has the sequence of SEQ ID NO:1.

In an aspect of the invention, the HIPO– cell has a reduced HLA-I function by virtue of a reduction in HLA-A protein expression. In another aspect, a gene encoding the HLA-A protein is knocked out. In another aspect, the HLA-I function is reduced by a reduction in HLA-B protein expression. In another aspect, a gene encoding the HLA-B protein is knocked out. In an aspect of the invention, the HIPO– cell has a reduced HLA-I function by virtue of a reduction in HLA-C protein expression. In another aspect, a gene encoding the HLA-C protein is knocked out. In another aspect, the HIPO– cell does not comprise an HLA-I function.

In an aspect of the invention, the HIPO– cell has a reduced HLA-II function by virtue of a reduction in CIITA protein expression. In another aspect, a gene encoding the CIITA protein is knocked out. In a preferred aspect, the CIITA protein has at least a 90% sequence identity to SEQ ID NO:2. In a more preferred aspect, the CIITA protein has the sequence of SEQ ID NO:2.

In an aspect of the invention, the HIPO– cell has a reduced HLA-II function by virtue of a reduction in HLA-DP protein expression. In another aspect, a gene encoding the HLA-DP protein is knocked out. In another aspect, the HLA-II function is reduced by a reduction in HLA-DR protein expression. In another aspect, a gene encoding the HLA-DR protein is knocked out. In another aspect, the HLA-II function is reduced by a reduction in HLA-DQ protein expression. In another aspect, a gene encoding the HLA-DQ protein is knocked out. In another aspect, the hypoimmunogenic pluripotent cell does not comprise an HLA-II function.

In an aspect of the invention, the hypoimmunogenic pluripotent cell has a reduced susceptibility to NK cell killing that is caused by an increased expression of a CD47 protein. In another aspect, the increased CD47 protein expression results from a modification to an endogenous CD47 gene locus. In another aspect, the increased CD47 protein expression results from a CD47 transgene. In a preferred aspect, the CD47 protein has at least a 90% sequence identity to SEQ ID NO:3. In a more preferred aspect, the CD47 protein has the sequence of SEQ ID NO:3.

In an aspect of the invention, the HIPO− cell further comprising a suicide gene that is activated by a trigger that causes the hypoimmunogenic pluripotent cell to die. In another aspect, the suicide gene is a herpes simplex virus thymidine kinase gene (HSV-tk) and the trigger is ganciclovir. In a preferred aspect, the HSV-tk gene encodes a protein comprising at least a 90% sequence identity to SEQ ID NO:4. In a more preferred aspect, the HSV-tk gene encodes a protein comprising the sequence of SEQ ID NO:4. In another aspect, the suicide gene is an *Escherichia coli* cytosine deaminase gene (EC-CD) and the trigger is 5-fluorocytosine (5-FC). In a preferred aspect, the EC-CD gene encodes a protein comprising at least a 90% sequence identity to SEQ ID NO:5. In a more preferred aspect, the EC-CD gene encodes a protein comprising the sequence of SEQ ID NO:5. In another aspect, the suicide gene encodes an inducible Caspase protein and the trigger is a chemical inducer of dimerization (CID). In a preferred aspect, the gene encodes an inducible Caspase protein comprising at least a 90% sequence identity to SEQ ID NO:6. In a more preferred aspect, the gene encodes an inducible Caspase protein comprising the sequence of SEQ ID NO:6. In another more preferred aspect, wherein the CID is AP1903.

The invention provides a cell derived from the HIPO− cells described herein, wherein the cells are selected from the group consisting of a chimeric antigen receptor (CAR) cell, an endothelial cell, a dopaminergic neuron, a pancreatic islet cell, and a retinal pigment endothelium cell. In a preferred aspect, the CAR cell is a CAR-T cell.

The invention provides a method, comprising transplanting a cell derived from the HIPO− cells described herein into a subject, wherein the subject is a human, cow, pig, chicken, turkey, horse, sheep, goat, donkey, mule, duck, goose, buffalo, camel, yak, llama, alpaca, mouse, rat, dog, cat, hamster, guinea pig.

In one aspect of the methods described herein, the cells derived from the HIPO− cells are selected from the group consisting of a chimeric antigen receptor (CAR) cell, an endothelial cell, a dopaminergic neuron, a pancreatic islet cell, and a retinal pigment endothelium cell.

The invention provides a method of treating a disease, comprising administering a cell derived from a HIPO− cell as described herein. In one aspect, the cell derived from the HIPO− cell is selected from the group consisting of a chimeric antigen receptor (CAR) cell, an endothelial cell, a dopaminergic neuron, a pancreatic islet cell, and a retinal pigment endothelium cell. In another aspect, the disease is selected from the group consisting of Type I Diabetes, a cardiac disease, a neurological disease, a cancer, an ocular disease, and a vascular disease.

The invention provides a method for generating a hypoimmunogenic pluripotent ABO group O Rh factor negative (HIPO−) cell from a parent cell comprising: eliminating the Major Histocompatibility Antigen Class I (HLA-I) function when compared to a parent pluripotent cell; eliminating the Major Histocompatibility Antigen Class II (HLA-I) function when compared to said parent pluripotent cell; increasing the expression of CD47 in the iPSC; eliminating an ABO blood group antigen resulting in ABO type O (O); and eliminating a Rhesus Factor (Rh) blood group antigen resulting in Rh type negative (−). In one aspect of the invention, the HIPO− cell has a human, cow, pig, chicken, turkey, horse, sheep, goat, donkey, mule, duck, goose, buffalo, camel, yak, llama, alpaca, mouse, rat, dog, cat, hamster, or guinea pig origin.

In another aspect, the ABO blood group type O results from eliminating an ABO blood group protein expression. In a preferred aspect, the ABO blood group has an eliminated blood group A or group B antigen expression because the parent cell is endogenously type O. In another aspect, the HIPO− cell is human and wherein the ABO blood group type O results from disrupting a human Exon 7 of the ABO gene.

In another aspect, the disruption in both alleles of Exon 7 of the ABO gene results from a Clustered Regularly Interspaced Short Palindromic Repeats)/Cas9 (CRISPR) reaction that disrupts both of the alleles.

In another aspect, the ABO blood group type O results from enzymaticly modifying an ABO gene product on a surface of the HIPO− cell. In a preferred aspect, the enzymatic modification removes a carbohydrate from the ABO gene product. In a more preferred aspect, the enzymatic modification removes a carbohydrate from an ABO A1 antigen, A2 antigen, or B antigen.

In another aspect of the invention, the Rh blood group has an eliminated Rh antigen expression because the parent cell is endogenously type Rh−. In another aspect, the method comprises eliminating an Rh protein expression. In a preferred aspect, the type Rh− results from disrupting a gene encoding Rh C antigen, Rh E antigen, Kell K antigen (KEL), Duffy (FY) Fya antigen, Duffy Fy3 antigen, Kidd (JK) Jkb antigen, or Kidd SLC14A1 gene. In another preferred aspect, the disruption results from a Clustered Regularly Interspaced Short Palindromic Repeats)/Cas9 (CRISPR) reaction that disrupts both alleles of the gene.

In another aspect of the invention, the methods disclosed herein results in an increased CD47 expression that results from introducing at least one copy of a human CD47 gene under the control of a promoter into the parent cell. In a preferred aspect, the promoter is a constitutive promoter.

In another aspect of the invention, the disruption in both alleles of the B2M gene results from a Clustered Regularly Interspaced Short Palindromic Repeats)/Cas9 (CRISPR) reaction that disrupts both of the B2M gene alleles. In another aspect, the disruption in both alleles of the CIITA gene results from a CRISPR reaction that disrupts both of the CIITA gene alleles. In another aspect, the HLA-I function is reduced by reducing the expression of a ß-2 microglobulin protein.

In another aspect of the invention, th HLA-I function is reduced or eliminated by reducing the ß-2 microglobulin protein expression. This may be done by knocking out a gene encoding the ß-2 microglobulin protein. In a preferred embodiment, the ß-2 microglobulin protein has at least a 90% sequence identity to SEQ ID NO:1. In a more preferred embodiment, the ß-2 microglobulin protein has the sequence of SEQ ID NO:1.

In another aspect of the invention, the HLA-I function is reduced by reducing the expression of HLA-A protein expression. In a preferred aspect, the HLA-A protein expression is reduced by knocking out a gene encoding the HLA-A protein. In another aspect, the HLA-I function is reduced by reducing the expression of HLA-B protein expression. In a preferred aspect the HLA-B protein expression is reduced by knocking out a gene encoding the HLA-B protein. In another aspect of the invention, the HLA-I function is reduced by reducing the expression of HLA-C protein expression. In a preferred aspect, the HLA-C protein expression is reduced by knocking out a gene encoding the HLA-C protein.

In an aspect of the invention, the methods disclosed herein result in a hypoimmunogenic pluripotent cell does not comprise an HLA-I function.

The invention provides methods as disclosed herein, wherein the HLA-II function is reduced by reducing the expression of a CIITA protein. In one aspect, the CIITA protein expression is reduced by knocking out a gene encoding the CIITA protein. In a preferred aspect, the CIITA protein has at least a 90% sequence identity to SEQ ID NO:2. In a more preferred aspect, the CIITA protein has the sequence of SEQ ID NO:2.

The invention provides methods as disclosed herein, wherein the HLA-II function is reduced by reducing the expression of an HLA-DP protein. In another aspect, the HLA-DP protein expression is reduced by knocking out a gene encoding the HLA-DP protein. In another aspect, the HLA-II function is reduced by reducing the expression of an HLA-DR protein. In another aspect, the HLA-DR protein expression is reduced by knocking out a gene encoding the HLA-DR protein. In another aspect, the HLA-II function is reduced by reducing the expression of an HLA-DQ protein. In another aspect, the HLA-DQ protein expression is reduced by knocking out a gene encoding the HLA-DQ protein.

In some aspects of the invention, the methods disclosed herein result in the hypoimmunogenic pluripotent cell does not comprise an HLA-II function.

The invention provides methods as disclosed herein, wherein the increased expression of a protein that reduces the susceptibility of the pluripotent cell to macrophage phagocytosis results from a modification to an endogenous gene locus. In some aspects, the endogenous gene locus encodes a CD47 protein. In another aspect, the increased protein expression results from the expression of a transgene. In another aspect, the transgene encodes a CD47 protein. In a preferred aspect, the CD47 protein has at least a 90% sequence identity to SEQ ID NO:3. In a more preferred aspect, the CD47 protein has the sequence of SEQ ID NO:3.

In an aspect of the invention, the method further comprises expressing a suicide gene that is activated by a trigger that causes the hypoimmunogenic pluripotent cell to die. In another aspect, the suicide gene is a herpes simplex virus thymidine kinase gene (HSV-tk) and the trigger is ganciclovir. In a preferred aspect, the HSV-tk gene encodes a protein comprising at least a 90% sequence identity to SEQ ID NO:4. In a more preferred aspect, the HSV-tk gene encodes a protein comprising the sequence of SEQ ID NO:4.

In another aspect of the invention, the suicide gene is an *Escherichia coli* cytosine deaminase gene (EC-CD) and the trigger is 5-fluorocytosine (5-FC). In a preferred aspect, the EC-CD gene encodes a protein comprising at least a 90% sequence identity to SEQ ID NO:5. In a more preferred aspect, the EC-CD gene encodes a protein comprising the sequence of SEQ ID NO:5.

In another aspect of the invention, the suicide gene encodes an inducible Caspase protein and the trigger is a specific chemical inducer of dimerization (CID). In a preferred aspect, the gene encodes an inducible Caspase protein comprising at least a 90% sequence identity to SEQ ID NO:6. In a more preferred aspect, the gene encodes an inducible Caspase protein comprising the sequence of SEQ ID NO:6. In another more preferred aspect, the CID is AP1903.

The invention provides an induced pluripotent cell comprising an ABO blood group type O (O) and a Rhesus Factor (Rh) blood type negative (−), wherein the induced pluripotent cell is less susceptible to rejection when transplanted into a subject when compared with an otherwise similar pluripotent cell that is an ABO blood group or Rh factor mismatch to the subject. In some aspects, the subject is selected from the group consisting of a human, cow, pig, chicken, turkey, horse, sheep, goat, donkey, mule, duck, goose, buffalo, camel, yak, llama, alpaca, mouse, rat, dog, cat, hamster, and guinea pig.

In one aspect of the invention, the induced pluripotent cell has an ABO blood group type O that results from a reduced ABO blood group protein expression. In another aspect, the ABO blood group is endogenously type O. In another aspect, the ABO blood group type O results from a disruption in human Exon 7 of the ABO gene.

In another aspect of the invention, the ABO blood group type O results from an enzymatic modification of an ABO gene product on a surface of the HIPO− cell. In a preferred aspect, the enzymatic modification removes a carbohydrate from the ABO gene product. In more preferred aspects, the enzymatic modification removes a carbohydrate from an ABO A1 antigen, A2 antigen, or B antigen.

In one aspect of the invention, the Rh blood group is endogenously type Rh−. In another aspect, n the Rh blood group results from a reduced Rh protein expression. In other aspects, the type Rh− results from a disruption in an Rh C antigen, an Rh E antigen, a Kell K antigen (KEL), a Duffy (FY) Fya antigen, a Duffy Fy3 antigen, a Kidd (JK) Jkb antigen, or a Kidd SLC14A1 gene.

The invention provides an embryonic stem cell comprising an an ABO blood group type O (O) and a Rhesus Factor (Rh) blood type negative (−), wherein the induced pluripotent cell is less susceptible to rejection when transplanted into a subject when compared with an otherwise similar pluripotent cell that is an ABO blood group or Rh factor mismatch to the subject. In some aspects, the subject is selected from the group consisting of a human, cow, pig, chicken, turkey, horse, sheep, goat, donkey, mule, duck, goose, buffalo, camel, yak, llama, alpaca, mouse, rat, dog, cat, hamster, and guinea pig.

In one aspect of the invention, the ABO blood group type O results from a reduced ABO blood group protein expression. In another aspect, the ABO blood group is endogenously type O. In another aspect, the ABO blood group type O results from a disruption in human Exon 7 of the ABO gene. In another aspect, the ABO blood group type O results from an enzymatic modification of an ABO gene product on a surface of the HIPO− cell. In a preferred aspect, the enzymatic modification removes a carbohydrate from the ABO gene product. In more preferred aspects, the enzymatic modification removes a carbohydrate from an ABO A1 antigen, A2 antigen, or B antigen.

In another aspect of the invention, the Rh blood group is endogenously type Rh−. In another aspect of the invention, the Rh blood group results from a reduced Rh protein expression. In other aspects of the invention, the type Rh− results from a disruption in an Rh C antigen, an Rh E antigen, a Kell K antigen (KEL), a Duffy (FY) Fya antigen, a Duffy Fy3 antigen, a Kidd (JK) Jkb antigen, or a Kidd SLC14A1 gene.

The invention provides a cell derived or differentiated from the induced ABO blood group O− Rh factor (−) pluripotent cells described herein. The invention also provides a cell derived or differentiated from the ABO blood group O− Rh factor (−) embryonic stem cells described herein.

V. BRIEF DESCRIPTION OF THE DRAWINGS

Immune assays using blood from Macaque Rhesus monkeys that rejected hypo-endothelial cells.

Figure 1B:
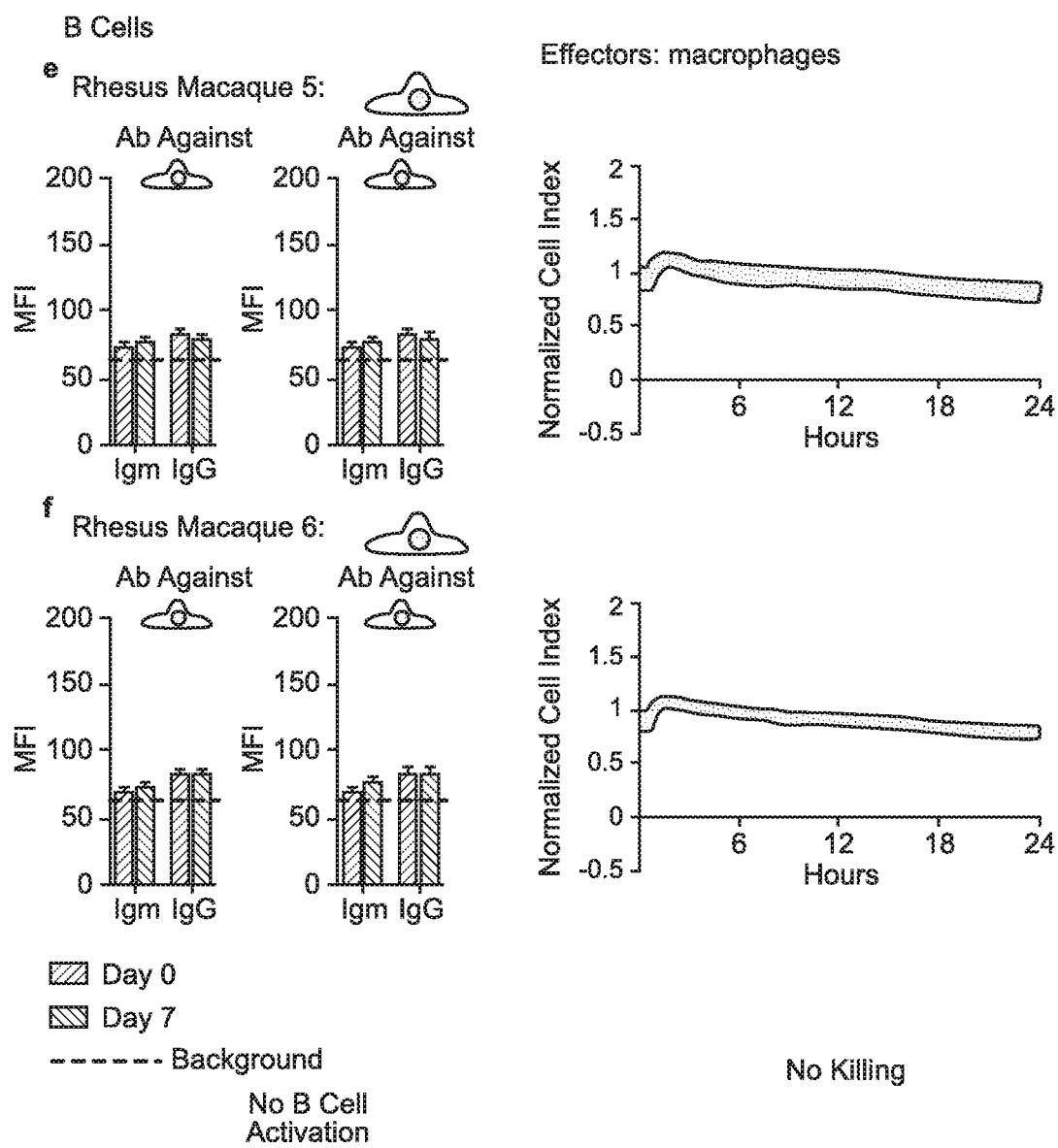

FIG. 1A shows adaptive and innate immune cells were not activated. Hypo-endothelial cells were not rejected by T cells, Cytotoxic T cells, or NK cells. FIG. 1B show that hypo-endothelial cells were not rejected by B cells or macrophages. Because the cells were cleared from the monkeys, another mechanism of rejection was suggested.

Figure 2:
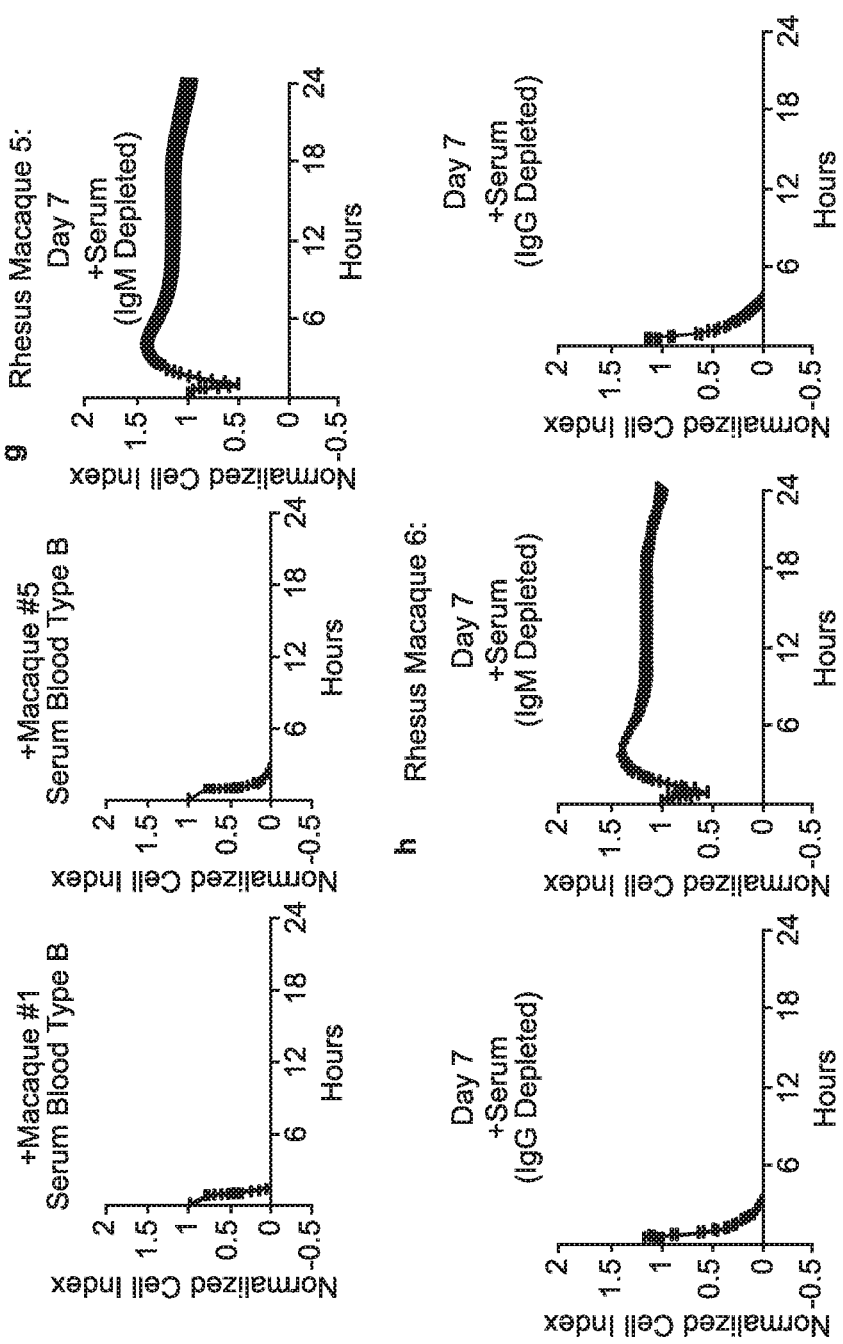

FIG. 2: Blood type rejection was confirmed by incubating human hypo-immunogenic endothelial cells with rhesus macaque serum. When human hypo-immunogenic endothelial cells (blood type A) are incubated with rhesus macaque serum (blood type B), cells are killed immediately. Depletion of either IgM or IgG antibodies demonstrated that the ABO− antibodies were from the IgM type.

Figure 3:
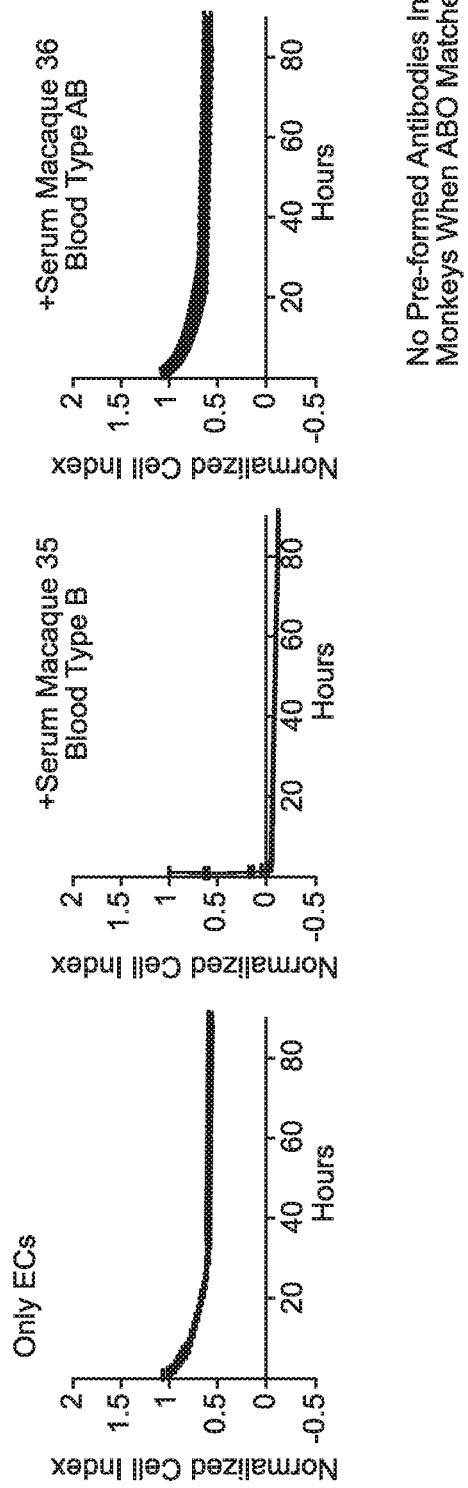

FIG. 3 shows that the human cells were not rejected by other pre-formed antibodies when transplanted across the xenogeneic barrier. Human HIP-derived endothelial cells (blood type A) were rejected when incubated with ABO− mismatched rhesus macaque serum (blood type B). When serum from rhesus macaque with blood type AB was used, however, the human cells survived (FIG. 3).

Figure 4:
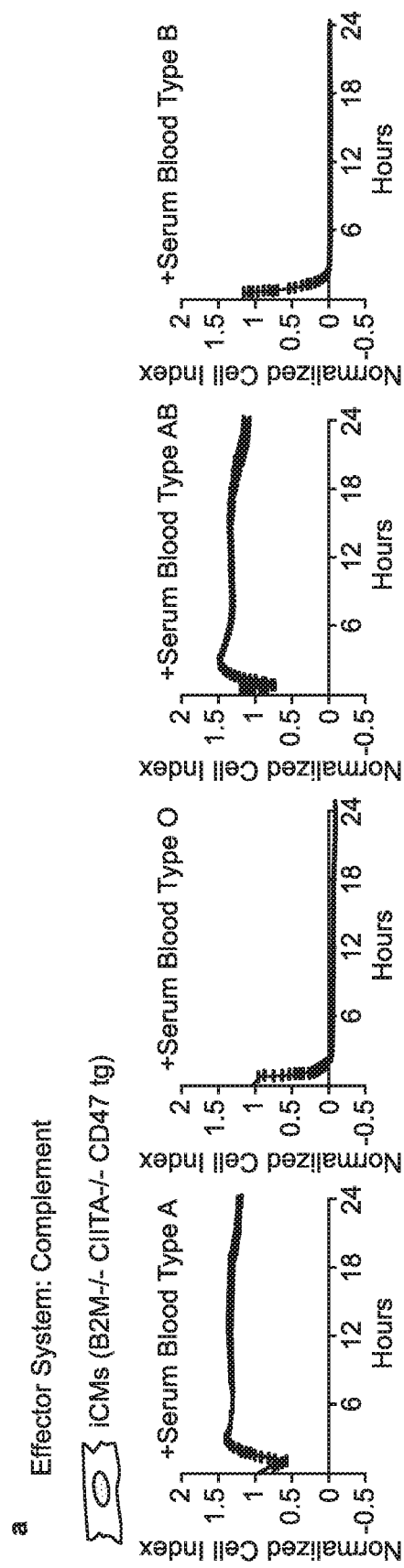

FIG. 4 shows that human hypo-immunogenic iPSC-derived endothelial cells (blood type A) survive when incubated with allogeneic human serum blood type A and AB. Serum containing pre-formed antibodies against A (blood type O and B), however, killed the cells immediately.

VI. DETAILED DESCRIPTION OF THE INVENTION

A. Introduction

The invention provides HypoImmunogenic Pluripotent Blood group O Rh− ("HIPO−") cells that avoid host immune responses due to several genetic or enzymatic manipulations as outlined herein. The cells lack major blood group and immune antigens that trigger immune responses and are engineered to avoid rejection, phagocytosis, or killing. This allows the derivation of "off-the-shelf" cell products for generating specific tissues and organs. The benefit of being able to use human allogeneic HIPO− cells and their derivatives in human patients provides significant benefits, including the ability to avoid long-term adjunct immunosuppressive therapy and drug use generally seen in allogeneic transplantations. It also provides significant cost savings as cell therapies can be used without requiring individual treatments for each patient. Recently, it was shown that cell products generated from autologous cell sources may become subject to immune rejection with few or even one single antigeneic mutation. Thus, autologous cell products are not inherently non-immunogenic. Also, cell engineering and quality control is very labor and cost intensive and autologous cells are not available for acute treatment options. Only allogeneic cell products will be able to be used for a bigger patient population if the immune hurdle can be overcome. HIPO− cells will serve as a universal cell source for the generation of universally-acceptable derivatives.

In addition to an O− blood type, the present invention, in part, exploits the fetomatemal tolerance that exists in pregnant women. Although half of a fetus' human leukocyte antigens (HLA) are paternally inherited and the fetus expresses major HLA mismatched antigens, the maternal immune system does not recognize the fetus as an allogeneic entity and does not initiate an immune response, e.g. as is seen in a "host versus graft" type of immune reaction. Fetomatemal tolerance is mainly mediated by syncytiotrophoblast cells in the fetal-maternal interface. Syncytiotrophoblast cells show little or no proteins of the major histocompatibility complexes I and II (MHC-I and MHC-II), as well as increased expression of CD47, known as the "don't eat me" protein that suppresses phagocytic innate immune surveillance and elimination of HLA-devoid cells. Surprisingly, the same tolerogenic mechanisms that prevent rejection of the fetus during pregnancy also allow the HIPO− cells of the invention to escape rejection and facilitate long-term survival and engrafiment of these cells after allogeneic transplantation.

Fetomatemal tolerance can be introduced with as little as three genetic modifications (as compared to the starting iPSCs, e.g. hiPSCs), two reductions in activity ("knock outs" as further described herein) and one increase in activity (a "knock in" as described herein). Generally, others of skill in the art have attempted to suppress immunogenicity of iPSCs but have been only partially successful; see Rong et al., *Cell Stem Cell* 14:121-130 (2014) and Gomalusse et al., *Nature Biotech* doi:10.1038/nbt.3860), WO2018/132783 and U.S. Prov. App. Nos. 62/698,941, 62/698,965, 62/698,973, 62/698,978, 62/698,981, and 62/698,984, each of which are incorporated by reference herein in their entirety.

Autologous induced pluripotent stem cells (iPSCs) constitute an unlimited cell source for patient-specific, autologous cell-based organ repair strategies. Their generation and subsequent differentiation into tissue cells, however, poses technical and manufacturing challenges and is a lengthy process that precludes their use in acute treatment modalities. These shortcomings can only be overcome with availability of prefabricated ready-to-use cell or tissue products of allogeneic origin.

The starter cell line for this approach, however, should be "universal". While HLA-matching can be achieved by HLA-knockouts (see the discussion above), ABO matching is challenging to be achieved by gene therapy. Because the universal blood type is O−, the invention provides for the first time HypoImmune Pluripotent O− ("HIPO−) cells, their maintenance, differentiation into desired cell and tissue types, and ultimately transplantation of their derivatives into patients in need thereof.

B. Definitions

The term "pluripotent cells" refers to cells that can self-renew and proliferate while remaining in an undifferentiated state and that can, under the proper conditions, be induced to differentiate into specialized cell types. The term "pluripotent cells," as used herein, encompass embryonic stem cells and other types of stem cells, including fetal, amnionic, or somatic stem cells. Exemplary human stem cell lines include the H9 human embryonic stem cell line. Additional exemplary stem cell lines include those made available through the National Institutes of Health Human Embryonic Stem Cell Registry and the Howard Hughes Medical Institute HUES collection (as described in Cowan, C. A. et. al, *New England J. Med.* 350:13. (2004), incorporated by reference herein in its entirety.)

"Pluripotent stem cells" as used herein have the potential to differentiate into any of the three germ layers: endoderm (e.g. the stomach linking, gastrointestinal tract, lungs, etc), mesoderm (e.g. muscle, bone, blood, urogenital tissue, etc) or ectoderm (e.g. epidermal tissues and nervous system tissues). The term "pluripotent stem cells," as used herein, also encompasses "induced pluripotent stem cells", or "iPSCs", a type of pluripotent stem cell derived from a non-pluripotent cell. Examples of parent cells include somatic cells that have been reprogrammed to induce a pluripotent, undifferentiated phenotype by various means. Such "iPS" or "iPSC" cells can be created by inducing the expression of certain regulatory genes or by the exogenous application of certain proteins. Methods for the induction of iPS cells are known in the art and are further described below. (See, e.g., Zhou et al., *Stem Cells* 27 (11): 2667-74 (2009); Huangfu et al., *Nature Biotechnol.* 26 (7): 795 (2008); Woltjen et al., *Nature* 458 (7239): 766-770 (2009); and Zhou et al., *Cell Stem Cell* 8:381-384 (2009); each of which is incorporated by reference herein in their entirety.) The generation of induced pluripotent stem cells (iPSCs) is outlined below. As used herein, "hiPSCs" are human induced pluripotent stem cells, and "miPSCs" are murine induced pluripotent stem cells.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least several, and in some embodiments, all of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics. As described herein, cells do not need to pass through pluripotency to be reprogrammed into endodermal progenitor cells and/or hepatocytes.

As used herein, "multipotent" or "multipotent cell" refers to a cell type that can give rise to a limited number of other particular cell types. For example, induced multipotent cells are capable of forming endodermal cells. Additionally, multipotent blood stem cells can differentiate itself into several types of blood cells, including lymphocytes, monocytes, neutrophils, etc.

As used herein, the term "oligopotent" refers to the ability of an adult stem cell to differentiate into only a few different cell types. For example, lymphoid or myeloid stem cells are capable of forming cells of either the lymphoid or myeloid lineages, respectively.

As used herein, the term "unipotent" means the ability of a cell to form a single cell type. For example, spermatogonial stem cells are only capable of forming sperm cells.

As used herein, the term "totipotent" means the ability of a cell to form an entire organism. For example, in mammals, only the zygote and the first cleavage stage blastomeres are totipotent.

As used herein, "non-pluripotent cells" refer to mammalian cells that are not pluripotent cells. Examples of such cells include differentiated cells as well as progenitor cells. Examples of differentiated cells include, but are not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, and T-cells. The starting cells employed for generating the induced multipotent cells, the endodermal progenitor cells, and the hepatocytes can be non-pluripotent cells.

Differentiated cells include, but are not limited to, multipotent cells, oligopotent cells, unipotent cells, progenitor cells, and terminally differentiated cells. In particular embodiments, a less potent cell is considered "differentiated" in reference to a more potent cell.

A "somatic cell" is a cell forming the body of an organism. Somatic cells include cells making up organs, skin, blood, bones and connective tissue in an organism, but not germ cells.

Cells can be from, for example, human or non-human mammals. Exemplary non-human mammals include, but are not limited to, mice, rats, cats, dogs, rabbits, guinea pigs, hamsters, sheep, pigs, horses, bovines, and non-human primates. In some embodiments, a cell is from an adult human or non-human mammal. In some embodiments, a cell is from a neonatal human, an adult human, or non-human mammal.

As used herein, the terms "subject" or "patient" refers to any animal, such as a domesticated animal, a zoo animal, or a human. The "subject" or "patient" can be a mammal like a dog, cat, bird, livestock, or a human. Specific examples of "subjects" and "patients" include, but are not limited to, individuals (particularly human) with a disease or disorder related to the liver, heart, lung, kidney, pancreas, brain, neural tissue, blood, bone, bone marrow, and the like.

Mammalian cells can be from humans or non-human mammals. Exemplary non-human mammals include, but are not limited to, mice, rats, cats, dogs, rabbits, guinea pigs, hamsters, sheep, pigs, horses, bovines, and non-human primates (e.g., chimpanzees, macaques, and apes).

By "hypo-immunogenic pluripotent" cell or "HIP" cell herein is meant a pluripotent cell that retains its pluripotent characteristics and yet gives rise to a reduced immunological rejection response when transferred into an allogeneic host. In preferred embodiments, HIP cells do not give rise to an immune response. Thus, "hypo-immunogenic" refers to a significantly reduced or eliminated immune response when compared to the immune response of a parental (i.e. "wt") cell prior to immunoengineering as outlined herein. In many cases, the HIP cells are immunologically silent and yet retain pluripotent capabilities. Assays for HIP characteristics are outlined below.

By "hypo-immunogenic pluripotent cell O–" "hypo-immunogenic pluripotent ORh–" cell or "HIPO–" cell herein is meant a HIP cell that is also ABO blood group 0 and Rhesus Factor Rh–. HIPO– cells may have been generated from O– cells, enzymatically modified to be O–, or genetically engineered to be O–.

By "HLA" or "human leukocyte antigen" complex is a gene complex encoding the major histocompatibility complex (MHC) proteins in humans. These cell-surface proteins that make up the HLA complex are responsible for the regulation of the immune response to antigens. In humans, there are two MHCs, class I and class II, "HLA-I" and "HLA-II". HLA-I includes three proteins, HLA-A, HLA-B and HLA-C, which present peptides from the inside of the cell, and antigens presented by the HLA-I complex attract killer T-cells (also known as CD8+ T-cells or cytotoxic T cells). The HLA-I proteins are associated with β-2 microglobulin (B2M). HLA-II includes five proteins, HLA-DP, HLA-DM, HLA-DOB, HLA-DQ and HLA-DR, which present antigens from outside the cell to T lymphocytes. This stimulates CD4+ cells (also known as T-helper cells). It should be understood that the use of either "MHC" or "HLA" is not meant to be limiting, as it depends on whether the genes are from humans (HLA) or murine (MHC). Thus, as it relates to mammalian cells, these terms may be used interchangeably herein.

By "gene knock out" herein is meant a process that renders a particular gene inactive in the host cell in which it resides, resulting either in no protein of interest being produced or an inactive form. As will be appreciated by those in the art and further described below, this can be accomplished in a number of different ways, including removing nucleic acid sequences from a gene, or interrupting the sequence with other sequences, altering the reading frame, or altering the regulatory components of the nucleic acid. For example, all or part of a coding region of the gene of interest can be removed or replaced with "nonsense" sequences, all or part of a regulatory sequence such as a promoter can be removed or replaced, translation initiation sequences can be removed or replaced, etc.

By "gene knock in" herein is meant a process that adds a genetic function to a host cell. This causes increased levels of the encoded protein. As will be appreciated by those in the art, this can be accomplished in several ways, including adding one or more additional copies of the gene to the host cell or altering a regulatory component of the endogenous gene increasing expression of the protein is made. This may be accomplished by modifying the promoter, adding a different promoter, adding an enhancer, or modifying other gene expression sequences.

"β-2 microglobulin" or "β2M" or "B2M" protein refers to the human β2M protein that has the amino acid and nucleic acid sequences shown below; the human gene has accession number NC_000015.10:44711487-44718159.

"CD47 protein" protein refers to the human CD47 protein that has the amino acid and nucleic acid sequences shown below; the human gene has accession number NC_000016.10:10866208-10941562.

"CIITA protein" protein refers to the human CIITA protein that has the amino acid and nucleic acid sequences shown below; the human gene has accession number NC_000003.12:108043094-108094200.

By "wild type" in the context of a cell means a cell found in nature. However, in the context of a pluripotent stem cell, as used herein, it also means an iPSC that may contain nucleic acid changes resulting in pluripotency but did not undergo the gene editing procedures of the invention to achieve hypo-immunogenicity.

By "syngeneic" herein refers to the genetic similarity or identity of a host organism and a cellular transplant where there is immunological compatibility; e.g. no immune response is generated.

By "allogeneic" herein refers to the genetic dissimilarity of a host organism and a cellular transplant where an immune response is generated.

By "B2M−/−" herein is meant that a diploid cell has had the B2M gene inactivated in both chromosomes. As described herein, this can be done in a variety of ways.

By "CIITA−/−" herein is meant that a diploid cell has had the CIITA gene inactivated in both chromosomes. As described herein, this can be done in a variety of ways.

By "CD47 tg" (standing for "transgene") or "CD47+") herein is meant that the host cell expresses CD47, in some cases by having at least one additional copy of the CD47 gene.

An "Oct polypeptide" refers to any of the naturally-occurring members of Octamer family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Oct polypeptides include Oct-1, Oct-2, Oct-3/4, Oct-6, Oct-7, Oct-8, Oct-9, and Oct-11. Oct3/4 (referred to herein as "Oct4") contains the POU domain, a 150 amino acid sequence conserved among Pit-1, Oct-1, Oct-2, and uric-86. (See, Ryan, A. K. & Rosenfeld, M. G., Genes Dev. 11:1207-1225 (1997), incorporated herein by reference in its entirety.) In some embodiments, variants have at least 85%, 90%, or 95% amino acid sequence identity across their whole sequence compared to a naturally occurring Oct polypeptide family member such as to those listed above or such as listed in Genbank accession number NP-002692.2 (human Oct4) or NP-038661.1 (mouse Oct4). Oct polypeptides (e.g., Oct3/4 or Oct 4) can be from human, mouse, rat, bovine, porcine, or other animals. Generally, the same species of protein will be used with the species of cells being manipulated. The Oct polypeptide(s) can be a pluripotency factor that can help induce multipotency in non-pluripotent cells.

A "Klf polypeptide" refers to any of the naturally-occurring members of the family of Krilppel-like factors (Klfs), zinc-finger proteins that contain amino acid sequences similar to those of the Drosophila embryonic pattern regulator Krilppel, or variants of the naturally-occurring members that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. (See, Dang, D. T., Pevsner, J. & Yang, V. W., Cell Biol. 32:1103-1121 (2000), incorporated by reference herein in its entirety.) Exemplary Klf family members include, Klf1, Klf2, Klf3, Klf-4, Klf5, Klf6, Klf7, Klf8, Klf9, Klf10, Klf11, Klf12, Klf13, Klf14, Klf15, Klf16, and Klf17. Klf2 and Klf-4 were found to be factors capable of generating iPS cells in mice, and related genes Klf1 and Klf5 did as well, although with reduced efficiency. (See, Nakagawa, et al., Nature Biotechnology 26:101-106 (2007), incorporated by reference herein in its entirety.) In some embodiments, variants have at least 85%, 90%, or 95% amino acid sequence identity across their whole sequence compared to a naturally occurring Klf polypeptide family member such as to those listed above or such as listed in Genbank accession number CAX16088 (mouse Klf4) or CAX14962 (human Klf4). Klf polypeptides (e.g., Klf1, Klf4, and Klf5) can be from human, mouse, rat, bovine, porcine, or other animals. Generally, the same species of protein will be used with the species of cells being manipulated. The Klf polypeptide(s) can be a pluripotency factor. The expression of the Klf4 gene or polypeptide can help induce multipotency in a starting cell or a population of starting cells.

A "Myc polypeptide" refers to any of the naturally-occurring members of the Myc family. (See. e.g., Adhikary, S. & Eilers, M., *Nat. Rev. Mol. Cell Biol.* 6:635-645 (2005), incorporated by reference herein in its entirety.) It also includes variants that maintain similar transcription factor activity when compared to the closest related naturally occurring family member (i.e. within at least 50%, 80%, or 90% activity). It further includes polypeptides comprising at least the DNA-binding domain of a naturally occurring family member, and can further comprise a transcriptional activation domain. Exemplary Myc polypeptides include, e.g., c-Myc, N-Myc and L-Myc. In some embodiments, variants have at least 85%, 90%, or 95% amino acid sequence identity across their whole sequence compared to a naturally occurring Myc polypeptide family member, such as to those listed above or such as listed in Genbank accession number CAA25015 (human Myc). Myc polypeptides (e.g., c-Myc) can be from human, mouse, rat, bovine, porcine, or other animals. Generally, the same species of protein will be used with the species of cells being manipulated. The Myc polypeptide(s) can be a pluripotency factor.

A "Sox polypeptide" refers to any of the naturally-occurring members of the SRY-related HMG-box (Sox) transcription factors, characterized by the presence of the high-mobility group (HMG) domain, or variants thereof that maintain similar transcription factor activity when compared to the closest related naturally occurring family member (i.e. within at least 50%, 80%, or 90% activity). It also includes polypeptides comprising at least the DNA-binding domain of the naturally occurring family member, and can further comprise a transcriptional activation domain. (See. e.g., Dang, D. T. et al., *Int. J. Biochem. Cell Biol.* 32:1103-1121 (2000), incorporated by reference herein in its entirety.) Exemplary Sox polypeptides include, e.g., Sox1, Sox-2, Sox3, Sox4, Sox5, Sox6, Sox7, Sox8, Sox9, Sox10, Sox11, Sox12, Sox13, Sox14, Sox15, Sox17, Sox18, Sox-21, and Sox30. Sox1 has been shown to yield iPS cells with a similar efficiency as Sox2, and genes Sox3, Sox15, and Sox18 have also been shown to generate iPS cells, although with somewhat less efficiency than Sox2. (See, Nakagawa, et al., *Nature Biotechnology* 26:101-106 (2007), incorporated by reference herein in its entirety.) In some embodiments, variants have at least 85%, 90%, or 95% amino acid sequence identity across their whole sequence compared to a naturally occurring Sox polypeptide family member such as to those listed above or such as listed in Genbank accession number CAA83435 (human Sox2). Sox polypeptides (e.g., Sox1, Sox2, Sox3, Sox15, or Sox18) can be from human, mouse, rat, bovine, porcine, or other animals. Generally, the same species of protein will be used with the species of cells being manipulated. The Sox polypeptide(s) can be a pluripotency factor. As discussed herein, SOX2 proteins find particular use in the generation of iPSCs.

By "differentiated hypo-immunogenic pluripotent cells" or "differentiated HIP cells" or "dHIP cells" herein is meant iPS cells that have been engineered to possess hypoimmunogenicity (e.g. by the knock out of B2M and CIITA and the knock in of CD47) and then are differentiated into a cell type for ultimate transplantation into subjects. Thus, for example HIP cells can be differentiated into hepatocytes ("dHIP hepatocytes"), into beta-like pancreatic cells or islet organoids ("dHIP beta cells"), into endothelial cells ("dHIP endothelial cells"), etc.

The term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

"Inhibitors," "activators," and "modulators" affect a function or expression of a biologically-relevant molecule. The term "modulator" includes both inhibitors and activators. They may be identified using in vitro and in vivo assays for expression or activity of a target molecule.

"Inhibitors" are agents that, e.g., inhibit expression or bind to target molecules or proteins. They may partially or totally block stimulation or have protease inhibitor activity. They may reduce, decrease, prevent, or delay activation, including inactivation, desensitizion, or down regulation of the activity of the described target protein. Modulators may be antagonists of the target molecule or protein.

"Activators" are agents that, e.g., induce or activate the function or expression of a target molecule or protein. They may bind to, stimulate, increase, open, activate, or facilitate the target molecule activity. Activators may be agonists of the target molecule or protein.

"Homologs" are bioactive molecules that are similar to a reference molecule at the nucleotide sequence, peptide sequence, functional, or structural level. Homologs may include sequence derivatives that share a certain percent identity with the reference sequence. Thus, in one embodiment, homologous or derivative sequences share at least a 70 percent sequence identity. In a specific embodiment, homologous or derivative sequences share at least an 80 or 85 percent sequence identity. In a specific embodiment, homologous or derivative sequences share at least a 90 percent sequence identity. In a specific embodiment, homologous or derivative sequences share at least a 95 percent sequence identity. In a more specific embodiment, homologous or derivative sequences share at least an 50, 55, 60, 65, 70, 75, 85, 86, 87, 88, 89, 90, 91, 92, 93, 94, 95, 96, 97, 98, or 99 percent sequence identity. Homologous or derivative nucleic acid sequences may also be defined by their ability to remain bound to a reference nucleic acid sequence under high stringency hybridization conditions. Homologs having a structural or functional similarity to a reference molecule may be chemical derivatives of the reference molecule. Methods of detecting, generating, and screening for structural and functional homologs as well as derivatives are known in the art.

"Hybridization" generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so.

For additional details and explanation of stringency of hybridization reactions, see Ausubel et al. Current Protocols in Molecular Biology, Wiley Interscience Publishers (1995), incorporated by reference herein in its entirety.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

"Stringent conditions" or "high stringency conditions", as defined herein, can be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 Mm sodium phosphate buffer at Ph 6.5 with 750 Mm sodium chloride, 75 Mm sodium citrate at 42° C.; or (3) overnight hybridization in a solution that employs 50% formamide, 5×SSC (0.75 M NaCl, 0.075 M sodium citrate), 50 Mm sodium phosphate (Ph 6.8), 0.1% sodium pyrophosphate, 5×Denhardt's solution, sonicated salmon sperm DNA (50 µl/ml), 0.1% SDS, and 10% dextran sulfate at 42° C., with a 10 minute wash at 42° C. in 0.2×SSC (sodium chloride/ sodium citrate) followed by a 10 minute high-stringency wash consisting of 0.1×SSC containing EDTA at 55° C.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein the term "modification" refers to an alteration that physically differentiates the modified molecule from the parent molecule. In one embodiment, an amino acid change in a CD47, HSVtk, EC-CD, or iCasp9 variant polypeptide prepared according to the methods described herein differentiates it from the corresponding parent that has not been modified according to the methods described herein, such as wild-type proteins, a naturally occurring mutant proteins or another engineered protein that does not include the modifications of such variant polypeptide. In another embodiment, a variant polypeptide includes one or more modifications that differentiates the function of the variant polypeptide from the unmodified polypeptide. For example, an amino acid change in a variant polypeptide affects its receptor binding profile. In other embodiments, a variant polypeptide comprises substitution, deletion, or insertion modifications, or combinations thereof. In another embodiment, a variant polypeptide includes one or more modifications that increases its affinity for a receptor compared to the affinity of the unmodified polypeptide.

In one embodiment, a variant polypeptide includes one or more substitutions, insertions, or deletions relative to a corresponding native or parent sequence. In certain embodiments, a variant polypeptide includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41 to 50, or 51 or more modifications.

By "episomal vector" herein is meant a genetic vector that can exist and replicate autonomously in the cytoplasm of a cell; e.g. it is not integrated into the genomic DNA of the host cell. A number of episomal vectors are known in the art and described below.

By "knock out" in the context of a gene means that the host cell harboring the knock out does not produce a functional protein product of the gene. As outlined herein, a knock out can result in a variety of ways, from removing all or part of the coding sequence, introducing frameshift mutations such that a functional protein is not produced (either truncated or nonsense sequence), removing or altering a regulatory component (e.g. a promoter) such that the gene is not transcribed, preventing translation through binding to mRNA, etc. Generally, the knock out is effected at the genomic DNA level, such that the cells' offspring also carry the knock out permanently.

By "knock in" in the context of a gene means that the host cell harboring the knock in has more functional protein active in the cell. As outlined herein, a knock in can be done in a variety of ways, usually by the introduction of at least one copy of a transgene (tg) encoding the protein into the cell, although this can also be done by replacing regulatory components as well, for example by adding a constitutive promoter to the endogeneous gene. In general, knock in technologies result in the integration of the extra copy of the transgene into the host cell.

VII. CELLS OF THE INVENTION

The invention provides compositions and methodologies for generating blood type O– pluripotent cells. In some aspects of the invention, the cells will be O– induced pluripotent stem cells (iPSCO–), O– embryonic stem cells (ESCO–), hypoimmunogenic pluripotent O– (HIPO–) cells, or cells derived or differentiated therefrom. In other aspects, the parent cell type is O–. In other aspects, the cells are modified enzymatically or genetically to the O– Rh– blood type.

A. Methodologies for Genetic Alterations

The invention includes methods of modifying nucleic acid sequences within cells or in cell-free conditions to generate both pluripotent cells and HIP cells. Exemplary technologies include homologous recombination, knock-in, ZFNs (zinc finger nucleases), TALENs (transcription activator-like effector nucleases), CRISPR (clustered regularly interspaced short palindromic repeats)/Cas9, and other site-specific nuclease technologies. These techniques enable double-strand DNA breaks at desired locus sites. These controlled double-strand breaks promote homologous recombination at the specific locus sites. This process focuses on targeting specific sequences of nucleic acid molecules, such as chromosomes, with endonucleases that recognize and bind to the sequences and induce a double-stranded break in the nucleic acid molecule. The double-strand break is repaired either by an error-prone non-homologous end-joining (NHEJ) or by homologous recombination (HR).

As will be appreciated by those in the art, a number of different techniques can be used to engineer the pluripotent cells of the invention, as well as the engineering of the iPSCs to become hypo-immunogenic as outlined herein.

In general, these techniques can be used individually or in combination. For example, in the generation of the HIP cells, CRISPR may be used to reduce the expression of active B2M and/or CIITA protein in the engineered cells, with viral techniques (e.g. lentivirus) to knock in the CD47 functionality. Also, as will be appreciated by those in the art, although one embodiment sequentially utilizes a CRISPR step to knock out B2M, followed by a CRISPR step to knock out CIITA with a final step of a lentivirus to knock in the CD47 functionality, these genes can be manipulated in different orders using different technologies.

As is discussed more fully below, transient expression of reprogramming genes is generally done to generate/induce pluripotent stem cells.

a. CRISPR Technologies

In one embodiment, the cells are manipulated using clustered regularly interspaced short palindromic repeats)/Cas ("CRISPR") technologies as is known in the art. CRISPR can be used to generate the starting iPSCs or to generate the HIP cells from the iPSCs. There are a large number of techniques based on CRISPR, see for example Doudna and Charpentier, Science doi:10.1126/science.1258096, hereby incorporated by reference. CRISPR techniques and kits are sold commercially.

b. TALEN Technologies

In some embodiments, the HIP cells of the invention are made using Transcription Activator-Like Effector Nucleases (TALEN) methodologies. TALEN are restriction enzymes combined with a nuclease that can be engineered to bind to and cut practically any desired DNA sequence. TALEN kits are sold commercially.

c. Zinc Finger Technologies

In one embodiment, the cells are manipulated using Zn finger nuclease technologies. Zn finger nucleases are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms, similar to CRISPR and TALENs.

d. Viral Based Technologies

There are a wide variety of viral techniques that can be used to generate the HIP cells of the invention (as well as for the original generation of the iPCSs), including, but not limited to, the use of retroviral vectors, lentiviral vectors, adenovirus vectors and Sendai viral vectors. Episomal vectors used in the generation of iPSCs are described below.

e. Down regulation of genes using interfering RNA

In other embodiments, genes that encode proteins used in HLA molecules are downregulated by RNAi technologies. RNA interference (RNAi) is a process where RNA molecules inhibit gene expression often by causing specific mRNA molecules to degrade. Two types of RNA molecules—microRNA (miRNA) and small interfering RNA (siRNA)—are central to RNA interference. They bind to the target mRNA molecules and either increase or decrease their activity. RNAi helps cells defend against parasitic nucleic acids such as those from viruses and transposons. RNAi also influences development.

sdRNA molecules are a class of asymmetric siRNAs comprising a guide (antisense) strand of 19-21 bases. They contain a 5' phosphate, 2'Ome or 2'F modified pyrimidines, and six phosphotioates at the 3' positions. They also contain a sense strand containing 3' conjugated sterol moieties, 2 phospotioates at the 3' position, and 2'Ome modified pyrimidines. Both strands contain 2' Ome purines with continuous stretches of unmodified purines not exceeding a length of 3. sdRNA is disclosed in U.S. Pat. No. 8,796,443, incorporated herein by reference in its entirety.

For all of these technologies, well known recombinant techniques are used, to generate recombinant nucleic acids as outlined herein. In certain embodiments, the recombinant nucleic acids (either than encode a desired polypeptide, e.g. CD47, or disruption sequences) may be operably linked to one or more regulatory nucleotide sequences in an expression construct. Regulatory nucleotide sequences will generally be appropriate for the host cell and subject to be treated. Numerous types of appropriate expression vectors and suitable regulatory sequences are known in the art for a variety of host cells. Typically, the one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are also contemplated. The promoters may be either naturally occurring promoters, or hybrid promoters that combine elements of more than one promoter. An expression construct may be present in a cell on an episome, such as a plasmid, or the expression construct may be inserted in a chromosome. In a specific embodiment, the expression vector includes a selectable marker gene to allow the selection of transformed host cells. Certain embodiments include an expression vector comprising a nucleotide sequence encoding a variant polypeptide operably linked to at least one regulatory sequence. Regulatory sequence for use herein include promoters, enhancers, and other expression control elements. In certain embodiments, an expression vector is designed for the choice of the host cell to be transformed, the particular variant polypeptide desired to be expressed, the vector's copy number, the ability to control that copy number, or the expression of any other protein encoded by the vector, such as antibiotic markers.

Examples of suitable mammalian promoters include, for example, promoters from the following genes: ubiquitin/S27a promoter of the hamster (WO 97/15664), Simian vacuolating virus 40 (SV40) early promoter, adenovirus major late promoter, mouse metallothionein-I promoter, the long terminal repeat region of Rous Sarcoma Virus (RSV), mouse mammary tumor virus promoter (MMTV), Moloney murine leukemia virus Long Terminal repeat region, and the early promoter of human Cytomegalovirus (CMV). Examples of other heterologous mammalian promoters are the actin, immunoglobulin or heat shock promoter(s).

In additional embodiments, promoters for use in mammalian host cells can be obtained from the genomes of viruses such as polyoma virus, fowlpox virus (UK 2,211,504 published 5 Jul. 1989), bovine papilloma virus, avian sarcoma virus, cytomegalovirus, a retrovirus, hepatitis-B virus and Simian Virus 40 (SV40). In further embodiments, heterologous mammalian promoters are used. Examples include the actin promoter, an immunoglobulin promoter, and heat-shock promoters. The early and late promoters of SV40 are conveniently obtained as an SV40 restriction fragment which also contains the SV40 viral origin of replication. Fiers et al., *Nature* 273: 113-120 (1978). The immediate early promoter of the human cytomegalovirus is conveniently obtained as a HindIII E restriction fragment. Greenaway, P. J. et al., *Gene* 18: 355-360 (1982). The foregoing references are incorporated by reference in their entirety.

B. Generation of Pluripotent Cells

The invention provides methods of producing non-immunogenic pluripotent cells from pluripotent cells. Thus, the first step is to provide the pluripotent stem cells.

The generation of mouse and human pluripotent stem cells (generally referred to as iPSCs; miPSCs for murine cells or hiPSCs for human cells) is generally known in the art. As will be appreciated by those in the art, there are a variety of different methods for the generation of iPCSs. The original induction was done from mouse embryonic or adult fibroblasts using the viral introduction of four transcription factors, Oct3/4, Sox2, c-Myc and Klf4; see Takahashi and Yamanaka Cell 126:663-676 (2006), hereby incorporated by reference in its entirety and specifically for the techniques outlined therein. Since then, a number of methods have been developed; see Seki et al., *World J. Stem Cells* 7(1):116-125 (2015) for a review, and Lakshmipathy and Vermuri, editors, Methods in Molecular Biology: Pluripotent Stem Cells. Methods and Protocols. Springer 2013, both of which are hereby expressly incorporated by reference in their entirety, and in particular for the methods for generating hiPSCs (see for example Chapter 3 of the latter reference).

Generally, iPSCs are generated by the transient expression of one or more "reprogramming factors" in the host cell, usually introduced using episomal vectors. Under these conditions, small amounts of the cells are induced to become iPSCs (in general, the efficiency of this step is low, as no selection markers are used). Once the cells are "reprogrammed", and become pluripotent, they lose the episomal vector(s) and produce the factors using the endogeneous genes. This loss of the episomal vector(s) results in cells that are called "zero footprint" cells. This is desirable as the fewer genetic modifications (particularly in the genome of the host cell), the better. Thus, it is preferred that the resulting hiPSCs have no permanent genetic modifications.

As is also appreciated by those of skill in the art, the number of reprogramming factors that can be used or are used can vary. Commonly, when fewer reprogramming factors are used, the efficiency of the transformation of the cells to a pluripotent state goes down, as well as the "pluripotency", e.g. fewer reprogramming factors may result in cells that are not fully pluripotent but may only be able to differentiate into fewer cell types.

In some embodiments, a single reprogramming factor, OCT4, is used. In other embodiments, two reprogramming factors, OCT4 and KLF4, are used. In other embodiments, three reprogramming factors, OCT4, KLF4 and SOX2, are used. In other embodiments, four reprogramming factors, OCT4, KLF4, SOX2 and c-Myc, are used. In other embodiments, 5, 6 or 7 reprogramming factors can be used selected from SOKMNLT; SOX2, OCT4 (POU5F1), KLF4, MYC, NANOG, LIN28, and SV40L T antigen.

In general, these reprogramming factor genes are provided on episomal vectors such as are known in the art and commercially available. For example, ThermoFisher/Invitrogen sell a sendai virus reprogramming kit for zero footprint generation of hiPSCs, see catalog number A34546. ThermoFisher also sells EBNA-based systems as well, see catalog number A14703.

In addition, there are a number of commercially available hiPSC lines available; see. e.g., the Gibco® Episomal hiPSC line, K18945, which is a zero footprint, viral-integration-free human iPSC cell line (see also Burridge et al, 2011, supra).

In general, as is known in the art, iPSCs are made from non-pluripotent cells such as CD34+ cord blood cells, fibroblasts, etc., by transiently expressing the reprogramming factors as described herein.

For example, successful iPSCs were also generated using only Oct3/4, Sox2 and Klf4, while omitting the C-Myc, although with reduced reprogramming efficiency.

In general, iPSCs are characterized by the expression of certain factors that include KLF4, Nanog, OCT4, SOX2, ESRRB, TBX3, c-Myc and TCL 1. New or increased expression of these factors for purposes of the invention may be via induction or modulation of an endogenous locus or from expression from a transgene.

For example, murine iPSCs can be generated using the methods of Diecke et al, *Sci Rep.* 2015, Jan. 28; 5:8081 (doi:10.1038/srep08081), hereby incorporated by reference in its entirety and specifically for the methods and reagents for the generation of the miPSCs. See also. e.g., Burridge et al., *PLoS One,* 20116(4):18293, hereby incorporated by reference in its entirety and specifically for the methods outlined therein.

In some cases, the pluripotency of the cells is measured or confirmed as outlined herein, for example by assaying for reprogramming factors or by conducting differentiation reactions as outlined herein and in the Examples.

C. Generation of Hypo-Immunogenic Pluripotent (HIP) Cells

Generating HIP cells from pluripotent cells is done with as few as three genetic changes, resulting in minimal disruption of cellular activity but conferring immunosilencing to the cells.

As discussed herein, one embodiment utilizes a reduction or elimination in the protein activity of MHC I and II (HLA I and II when the cells are human). This can be done by altering genes encoding their component. In one embodiment, the coding region or regulatory sequences of the gene are disrupted using CRISPR. In another embodiment, gene translation is reduced using interfering RNA technologies. The third change is a change in a gene that regulates susceptibility to macrophage phagocytosis, such as CD47, and this is generally a "knock in" of a gene using viral technologies.

In some cases, where CRISPR is being used for the genetic modifications, hiPSC cells that contain a Cas9 construct that enable high efficiency editing of the cell line can be used; see. e.g., the Human Episomal Cas9 iPSC cell line, A33124, from Life Technologies.

1. HLA-I Reduction

The HIP cells of the invention include a reduction in MHC I function (HLA I when the cells are derived from human cells).

As will be appreciated by those in the art, the reduction in function can be accomplished in a number of ways, including removing nucleic acid sequences from a gene, interrupting the sequence with other sequences, or altering the regulatory components of the nucleic acid. For example, all or part of a coding region of the gene of interest can be removed or replaced with "nonsense" sequences, frameshift mutations can be made, all or part of a regulatory sequence such as a promoter can be removed or replaced, translation initiation sequences can be removed or replaced, etc.

As will be appreciated by those in the art, the successful reduction of the MHC I function (HLA I when the cells are derived from human cells) in the pluripotent cells can be measured using techniques known in the art and as described below; for example, FACS techniques using labeled antibodies that bind the HLA complex; for example, using commercially available HLA-A,B,C antibodies that bind to the the alpha chain of the human major histocompatibility HLA Class I antigens.

a. B2M Alteration

In one embodiment, the reduction in HLA-I activity is done by disrupting the expression of the β-2 microglobulin gene in the pluripotent stem cell, the human sequence of which is disclosed herein. This alteration is generally referred to herein as a gene "knock out", and in the HIP cells of the invention it is done on both alleles in the host cell. Generally the techniques to do both disruptions is the same.

A particularly useful embodiment uses CRISPR technology to disrupt the gene. In some cases, CRISPR technology is used to introduce small deletions/insertions into the coding region of the gene, such that no functional protein is produced, often the result of frameshift mutations that result in the generation of stop codons such that truncated, non-functional proteins are made.

Accordingly, a useful technique is to use CRISPR sequences designed to target the coding sequence of the B2M gene in mouse or the B2M gene in human. After gene editing, the transfected iPSC cultures are dissociated to single cells. Single cells are expanded to full-size colonies and tested for CRISPR edit by screening for presence of aberrant sequence from the CRISPR cleavage site. Clones with deletions in both alleles are picked. Such clones did not express B2M as demonstrated by PCR and did not express HLA-I as demonstrated by FACS analysis (see examples 1 and 6, for example).

Assays to test whether the B2M gene has been inactivated are known and described herein. In one embodiment, the assay is a Western blot of cells lysates probed with antibodies to the B2M protein. In another embodiment, reverse transcriptase polymerase chain reactions (rt-PCR) confirms the presence of the inactivating alteration.

In addition, the cells can be tested to confirm that the HLA I complex is not expressed on the cell surface. This may be assayed by FACS analysis using antibodies to one or more HLA cell surface components as discussed above.

It is noteworthy that others have had poor results when trying to silence the B2M genes at both alleles. See. e.g. Gomalusse et al., *Nature Biotech*. Doi/10.1038/nbt.3860).

2. HLA-II Reduction

In addition to a reduction in HLA I, the HIP cells of the invention also lack MHC II function (HLA II when the cells are derived from human cells).

As will be appreciated by those in the art, the reduction in function can be accomplished in a number of ways, including removing nucleic acid sequences from a gene, adding nucleic acid sequences to a gene, disrupting the reading frame, interrupting the sequence with other sequences, or altering the regulatory components of the nucleic acid. In one embodiment, all or part of a coding region of the gene of interest can be removed or replaced with "nonsense" sequences. In another embodiment, regulatory sequences such as a promoter can be removed or replaced, translation initiation sequences can be removed or replaced, etc.

The successful reduction of the MHC II function (HLA II when the cells are derived from human cells) in the pluripotent cells or their derivatives can be measured using techniques known in the art such as Western blotting using antibodies to the protein, FACS techniques, rt-PCR techniques, etc.

a. CIITA Alteration

In one embodiment, the reduction in HLA-II activity is done by disrupting the expression of the CIITA gene in the pluripotent stem cell, the human sequence of which is shown herein. This alteration is generally referred to herein as a gene "knock out", and in the HIP cells of the invention it is done on both alleles in the host cell.

Assays to test whether the CIITA gene has been inactivated are known and described herein. In one embodiment, the assay is a Western blot of cells lysates probed with antibodies to the CIITA protein. In another embodiment, reverse transcriptase polymerase chain reactions (rt-PCR) confirms the presence of the inactivating alteration.

In addition, the cells can be tested to confirm that the HLA II complex is not expressed on the cell surface. Again, this assay is done as is known in the art. Exemplary analyses include Western Blots or FACS analysis using commercial antibodies that bind to human HLA Class II HLA-DR, DP and most DQ antigens as outlined below.

A particularly useful embodiment uses CRISPR technology to disrupt the CIITA gene. CRISPRs were designed to target the coding sequence of the Ciita gene in mouse or the CIITA gene in human, an essential transcription factor for all MHC II molecules. After gene editing, the transfected iPSC cultures were dissociated into single cells. They were expanded to full-size colonies and tested for successful CRISPR editing by screening for the presence of an aberrant sequence from the CRISPR cleavage site. Clones with deletions did not express CIITA as determined by PCR and did not express MHC II/HLA-II as determined by FACS analysis.

3. Phagocytosis Reduction

In addition to the reduction of HLA I and II (or MHC I and II), generally using B2M and CIITA knock-outs, the HIP cells of the invention have a reduced susceptibility to macrophage phagocytosis and NK cell killing. The resulting HIP cells "escape" the immune macrophage and innate pathways due to one or more CD47 transgenes.

a. CD47 Increase

In some embodiments, reduced macrophage phagocytosis and NK cell killing susceptibility results from increased CD47 on the HIP cell surface. This is done in several ways as will be appreciated by those in the art using "knock in" or transgenic technologies. In some cases, increased CD47 expression results from one or more CD47 transgene.

Accordingly, in some embodiments, one or more copies of a CD47 gene is added to the HIP cells under control of an inducible or constitutive promoter, with the latter being preferred. In some embodiments, a lentiviral construct is employed as described herein or known in the art. CD47 genes may integrate into the genome of the host cell under the control of a suitable promoter as is known in the art.

The HIP cell lines were generated from B2M−/− CIITA−/− iPSCs. Cells containing lentivirus vectors expressing CD47 were selected using a Blasticidin marker. The CD47 gene sequence was synthesized and the DNA was cloned into the plasmid Lentivirus pLenti6N5 with a blasticidin resistance (ermo Fisher Scientific, Waltham, Mass.)

In some embodiments, the expression of the CD47 gene can be increased by altering the regulatory sequences of the endogenous CD47 gene, for example, by exchanging the endogenous promoter for a constitutive promoter or for a different inducible promoter. This can generally be done using known techniques such as CRISPR.

Once altered, the presence of sufficient CD47 expression can be assayed using known techniques such as those described in the Examples, such as Western blots, ELISA assays or FACS assays using anti-CD47 antibodies. In general, "sufficiency" in this context means an increase in the expression of CD47 on the HIP cell surface that silences NK cell killing. The natural expression levels on cells is too low to protect them from NK cell lysis once their MHC I is removed.

4. Suicide Genes

In some embodiments, the invention provides hypoimmunogenic pluripotent cells that comprise a "suicide gene" or "suicide switch". These are incorporated to function as a "safety switch" that can cause the death of the hypoimmunogenic pluripotent cells should they grow and divide in an undesired manner. The "suicide gene" ablation approach includes a suicide gene in a gene transfer vector encoding a protein that results in cell killing only when activated by a specific compound. A suicide gene may encode an enzyme that selectively converts a nontoxic compound into highly toxic metabolites. The result is specifically eliminating cells expressing the enzyme. In some embodiments, the suicide gene is the herpesvirus thymidine kinase (HSV-tk) gene and the trigger is ganciclovir. In other embodiments, the suicide gene is the *Escherichia coli* cytosine deaminase (EC-CD) gene and the trigger is 5-fluorocytosine (5-FC) (Barese et al., *Mol. Therap.* 20(10):1932-1943 (2012), Xu et al., *Cell Res.* 8:73-8 (1998), both incorporated herein by reference in their entirety.)

In other embodiments, the suicide gene is an inducible Caspase protein. An inducible Caspase protein comprises at least a portion of a Caspase protein capable of inducing apoptosis. In one embodiment, the portion of the Caspase protein is exemplified in SEQ ID NO:6. In preferred embodiments, the inducible Caspase protein is iCasp9. It comprises the sequence of the human FK506-binding protein, FKBP12, with an F36V mutation, connected through a series of amino acids to the gene encoding human caspase 9. FKBP12-F36V binds with high affinity to a small-molecule dimerizing agent, AP1903. Thus, the suicide function of iCasp9 in the instant invention is triggered by the administration of a chemical inducer of dimerization (CID). In some embodiments, the CID is the small molecule drug AP1903. Dimerization causes the rapid induction of apoptosis. (See WO2011146862; Stasi et al, *N. Engl. J. Med* 365; 18 (2011); Tey et al., *Biol. BloodMarrow Transplant.* 13:913-924 (2007), each of which are incorporated by reference herein in their entirety.)

5. Assays for HIP Phenotypes and Retention of Pluripotency

Once the HIP cells have been generated, they may be assayed for their hypo-immunogenicity and/or retention of pluripotency as is generally described herein and in the examples.

For example, hypo-immunogenicity are assayed using a number of techniques One exemplary technique includes transplantation into allogeneic hosts and monitoring for HIP cell growth (e.g. teratomas) that escape the host immune system. HIP derivatives are transduced to express luciferase and can then followed using bioluminescence imaging. Similarly, the T cell and/or B cell response of the host animal to the HIP cells are tested to confirm that the HIP cells do not cause an immune reaction in the host animal. T cell function is assessed by Elispot, Elisa, FACS, PCR, or mass cytometry (CYTOF). B cell response or antibody response is assessed using FACS or luminex. Additionally, or alternatively, the cells may be assayed for their ability to avoid innate immune responses, e.g. NK cell killing. NK cell lytolytic activity is assessed in vitro or in vivo using techniques known in the art.

Similarly, the retention of pluripotency is tested in a number of ways. In one embodiment, pluripotency is assayed by the expression of certain pluripotency-specific factors as generally described herein. Additionally or alternatively, the HIP cells are differentiated into one or more cell types as an indication of pluripotency.

D. Generation of Hypo-Immunogenic Pluripotent O– Cells

In some aspects of the invention, the HIP cells generated as above will already be HIPO– cells because the process will have started with pluripotent cells having an O– blood type.

Other aspects of the invention involve the enzymatic conversion of A and B antigens. In preferred aspects, the B antigen is converted to O using an enzyme. In more preferred aspects, the enzyme is an α-galactosidase. This enzyme eliminates the terminal galactose residue of the B antigen. Other aspects of the invention involve the enzymatic conversion of A antigen to O. In preferred aspects, the A antigen is converted to O using an α-N-acetylgalactosaminidase. Enzymatic conversion is discussed, e.g., in Olsson et al., *Transfusion Clinique et Biologique* 11:33-39 (2004); U.S. Pat. Nos. 4,427,777, 5,606,042, 5,633,130, 5,731,426, 6,184,017, 4,609,627, and 5,606,042; and Int'l Pub. No. WO9923210, each of which are incorporated by reference herein in their entirety.

Other embodiments of the invention involve genetically engineering the cells by knocking out the ABO gene Exon 7 or silencing the SLC14A1 (JK) gene. Other embodiments of the invention involve knocking out the C and E antigens of the Rh blood group system (RH), K in the Kell system (KEL), Fya and Fy3 in the Duffy system (FY), Jkb in the Kidd system (K), or U and S in the MNS blood group system. Any knockout methodology known in the art or described herein, such as CRISPR, talens, or homologous recombination, may be employed.

E. Preferred Embodiments of the Invention

The HIPO–, iPSCO–, or ESCO– cells, or derivatives thereof, of the invention may be used to treat, for example, Type 1 diabetes, cardiac diseases, neurological diseases, cancer, blindness, vascular diseases, and others that respond to regenerative medicine therapies. In particular, the invention contemplates using the HIPO– cells for differentiation into any cell type. Thus, provided herein are HIPO– cells that exhibit pluripotency but do not result in a host immune response when transplanted into an allogeneic host such as a human patient, either as the HIPO– cells or as the differentiated products of the HIPO– cells.

In one aspect, the present invention provides an isolated hypoimmunogenic or hypoimmune pluripotent stem cell (HIPO– cell) comprising a nucleic acid encoding a chimeric antigen receptor (CAR), wherein endogenous β-2 microglobulin (B2M) gene activity and endogenous class II transactivator (CIITA) gene activity have been eliminated and CD47 expression has been increased. The CAR can comprise an extracellular domain, a transmembrane domain, and an intracellular signaling domain.

In some embodiments, the extracellular domain binds to an antigen selected from the group consisting of CD19, CD20, CD22, CD38, CD123, CS1, CD171, BCMA, MUC16, ROR1, and WT1. In certain embodiments, the extracellular domain comprises a single chain variable fragment (scFv). In some embodiments, the transmembrane domain comprises CD3ζ, CD4, CD8α, CD28, 4-1BB, OX40, ICOS, CTLA-4, PD-1, LAG-3, and BTLA. In certain embodiments, the intracellular signaling domain comprises CD3ζ, CD28, 4-1BB, OX40, ICOS, CTLA-4, PD-1, LAG-3, and BTLA.

In certain embodiments, the CAR comprises an anti-CD19 scFv domain, a CD28 transmembrane domain, and a CD3 zeta signaling intracellular domain. In some embodiments, the CAR comprises anti-CD19 scFv domain, a CD28 transmembrane domain, a 4-1BB signaling intracellular domain, and a CD3 zeta signaling intracellular domain.

In another aspect of the invention, provided is an isolated hypoimmune CAR-T (HI-CAR-T) cell produced by in vitro differentiation of any one of the HIPO− cells described herein. In some embodiments, the HIO-CAR-T cell is a cytotoxic hypoimmune O− CAR-T cell.

In various embodiments, the in vitro differentiation comprises culturing the HIPO− cell carrying a CAR construct in a culture media comprising one or more growth factors or cytokines selected from the group consisting of bFGF, EPO, Flt3L, IGF, IL-3, IL-6, IL-15, GM-CSF, SCF, and VEGF. In some embodiments, the culture media further comprises one or more selected from the group consisting of a BMP activator, a GSK3 inhibitor, a ROCK inhibitor, a TGFβ receptor/ALK inhibitor, and a NOTCH activator.

In particular embodiments, isolated hypoimmune O− (HIO-CAR-T) cell produced by in vitro differentiation of any one of the HIPO− carrying the CAR-T construct is for use as a treatment of cancer.

In another aspect of the invention, provided is a method of treating a patient with cancer by administering a composition comprising a therapeutically effective amount of any of the isolated HIO-CAR-T cells described herein. In some embodiments, the composition further comprises a therapeutically effective carrier.

In some embodiments, the administration step comprises intravenous administration, subcutaneous administration, intranodal administration, intratumoral administration, intrathecal administration, intrapleural administration, and intraperitoneal administration. In certain instances, the administration further comprises a bolus or by continuous perfusion.

In some embodiments, the cancer is a blood cancer selected from the group consisting of leukemia, lymphoma, and myeloma. In various embodiments, the cancer is a solid tumor cancer or a liquid tumor cancer.

In another aspect, the present invention provides a method of making any one of the isolated HIO-CAR-T cells described herein. The method includes in vitro differentiating of any one of the HIPO− cells of the invention wherein in vitro differentiating comprises culturing the HIPO− cell in a culture media comprising one or more growth factors or cytokines selected from the group consisting of bFGF, EPO, Flt3L, IGF, IL-2, IL-3, IL-6, IL-7, IL-15, GM-CSF, SCF, and VEGF. In some embodiments, the culture media further comprises one or more selected from the group consisting of a BMP activator, a GSK3 inhibitor, a ROCK inhibitor, a TGFβ receptor/ALK inhibitor, and a NOTCH activator.

In some embodiments, the in vitro differentiating comprises culturing the HIPO− cells on feeder cells. In various embodiments, the in vitro differentiating comprises culturing in simulated microgravity. In certain instances, the culturing in simulated microgravity is for at least 72 hours.

In some aspects, provided herein is an isolated, engineered hypoimmune cardiac cell (hypoimmunogenic cardiac cell) differentiated from a HIPO− cell.

In some aspects, provided herein is a method of treating a patient suffering from a heart condition or disease. The method comprises administering a composition comprising a therapeutically effective amount of a population of any one of the isolated, engineered hypoimmune cardiac cells derived from HIPO− cells as described herein. In some embodiments, the composition further comprises a therapeutically effective carrier.

In some embodiments, the administration comprises implantation into the patient's heart tissue, intravenous injection, intraarterial injection, intracoronary injection, intramuscular injection, intraperitoneal injection, intramyocardial injection, trans-endocardial injection, trans-epicardial injection, or infusion.

In some embodiments, the heart condition or disease is selected from the group consisting of pediatric cardiomyopathy, age-related cardiomyopathy, dilated cardiomyopathy, hypertrophic cardiomyopathy, restrictive cardiomyopathy, chronic ischemic cardiomyopathy, peripartum cardiomyopathy, inflammatory cardiomyopathy, other cardiomyopathy, myocarditis, myocardial ischemic reperfusion injury, ventricular dysfunction, heart failure, congestive heart failure, coronary artery disease, end stage heart disease, atherosclerosis, ischemia, hypertension, restenosis, angina pectoris, rheumatic heart, arterial inflammation, or cardiovascular disease.

In some aspects, provided herein is a method of producing a population of hypoimmune cardiac cells from a population of HIPO− cells by in vitro differentiation, wherein endogenous β-2 microglobulin (B2M) gene activity and endogenous class II transactivator (CIITA) gene activity have been eliminated and CD47 expression has been increased in the HIPO− cells. The method comprises: (a) culturing a population of HIPO− cells in a culture medium comprising a GSK inhibitor; (b) culturing the population of HIPO− cells in a culture medium comprising a WNT antagonist to produce a population of pre-cardiac cells; and (c) culturing the population of pre-cardiac cells in a culture medium comprising insulin to produce a population of hypoimmune cardiac cells.

In some embodiments, the GSK inhibitor is CHIR-99021, a derivative thereof, or a variant thereof. In some instances, the GSK inhibitor is at a concentration ranging from about 2 μM to about 10 μM. In some embodiments, the WNT antagonist is IWR1, a derivative thereof, or a variant thereof. In some instances, the WNT antagonist is at a concentration ranging from about 2 μM to about 10 μM.

In some aspects, provided herein is an isolated, engineered hypoimmune endothelial cell differentiated from HIPO− cells. In other aspects, the isolated, engineered hypoimmune endothelial cell is selected from the group consisting of a capillary endothelial cell, vascular endothelial cell, aortic endothelial cell, brain endothelial cell, and renal endothelial cell.

In some aspects, provided herein is a method of treating a patient suffering from a vascular condition or disease. In some embodiments, the method comprises administering a composition comprising a therapeutically effective amount of a population of isolated, engineered hypoimmune endothelial cells.

The method comprises administering a composition comprising a therapeutically effective amount of a population of any one of the isolated, engineered hypoimmune endothelial cells described herein. In some embodiments, the composition further comprises a therapeutically effective carrier. In some embodiments, the administration comprises implantation into the patient's heart tissue, intravenous injection, intraarterial injection, intracoronary injection, intramuscular injection, intraperitoneal injection, intramyocardial injection, trans-endocardial injection, trans-epicardial injection, or infusion.

In some embodiments, the vascular condition or disease is selected from the group consisting of, vascular injury, cardiovascular disease, vascular disease, ischemic disease, myocardial infarction, congestive heart failure, hypertension, ischemic tissue injury, limb ischemia, stroke, neuropathy, and cerebrovascular disease.

In some aspects, provided herein is a method of producing a population of hypoimmune endothelial cells from a population of HIPO− cells by in vitro differentiation, wherein endogenous β-2 microglobulin (B2M) gene activity and endogenous class II transactivator (CIITA) gene activity have been eliminated and CD47 expression has been increased in the HIPO− cells. The method comprises: (a) culturing a population of HIPO− cells in a first culture medium comprising a GSK inhibitor; (b) culturing the population of HIPO− cells in a second culture medium comprising VEGF and bFGF to produce a population of pre-endothelial cells; and (c) culturing the population of pre-endothelial cells in a third culture medium comprising a ROCK inhibitor and an ALK inhibitor to produce a population of hypoimmune endothelial cells.

In some embodiments, the GSK inhibitor is CHIR-99021, a derivative thereof, or a variant thereof. In some instances, the GSK inhibitor is at a concentration ranging from about 1 µM to about 10 µM. In some embodiments, the ROCK inhibitor is Y-27632, a derivative thereof, or a variant thereof. In some instances, the ROCK inhibitor is at a concentration ranging from about 1 µM to about 20 µM. In some embodiments, the ALK inhibitor is SB-431542, a derivative thereof, or a variant thereof. In some instances, the ALK inhibitor is at a concentration ranging from about 0.5 µM to about 10 µM.

In some embodiments, the first culture medium comprises from 2 µM to about 10 µM of CHIR-99021. In some embodiments, the second culture medium comprises 50 ng/ml VEGF and 10 ng/ml bFGF. In other embodiments, the second culture medium further comprises Y-27632 and SB-431542. In various embodiments, the third culture medium comprises 10 µM Y-27632 and 1 µM SB-431542. In certain embodiments, the third culture medium further comprises VEGF and bFGF. In particular instances, the first culture medium and/or the second medium is absent of insulin.

In some aspects, provided herein is an isolated, engineered hypoimmune dopaminergic neuron (DN) differentiated from a hypoimmune pluripotent cell (HIPO− cell), wherein endogenous β-2 microglobulin (B2M) gene activity and endogenous class II transactivator (CIITA) gene activity have been eliminated, CD47 expression has been increased, the neuron is blood type O and Rh−.

In some embodiments, the isolated hypoimmune dopaminergic neuron is selected from the group consisting of a neuronal stem cell, neuronal progenitor cell, immature dopaminergic neuron, and mature dopaminergic neuron.

In some aspects, provided herein is a method of treating a patient suffering from a neurodegenerative disease or condition. In some embodiments, the method comprises administering a composition comprising a therapeutically effective amount of a population of any one of the isolated hypoimmune dopaminergic neurons. In some embodiments, the composition further comprises a therapeutically effective carrier. In some embodiments, the population of the isolated hypoimmune dopaminergic neurons is on a biodegradable scaffold. The administration may comprise transplantation or injection. In some embodiments, the neurodegenerative disease or condition is selected from the group consisting of Parkinson's disease, Huntington disease, and multiple sclerosis.

In some aspects, provided herein is a method of producing a population of hypoimmune dopaminergic neurons from a population of HIPO− cells by in vitro differentiation, wherein endogenous β-2 microglobulin (B2M) gene activity and endogenous class II transactivator (CIITA) gene activity have been eliminated, CD47 expression has been increased, the blood group is O and Rh− in the HIPO− cells. In some embodiments, the method comprises (a) culturing the population of HIPO− cells in a first culture medium comprising one or more factors selected from the group consisting of sonic hedgehog (SHH), BDNF, EGF, bFGF, FGF8, WNT1, retinoic acid, a GSK3β inhibitor, an ALK inhibitor, and a ROCK inhibitor to produce a population of immature dopaminergic neurons; and (b) culturing the population of immature dopaminergic neurons in a second culture medium that is different than the first culture medium to produce a population of dopaminergic neurons.

In some embodiments, the GSKβ inhibitor is CHIR-99021, a derivative thereof, or a variant thereof. In some instances, the GSKβ inhibitor is at a concentration ranging from about 2 µM to about 10 µM. In some embodiments, the ALK inhibitor is SB-431542, a derivative thereof, or a variant thereof. In some instances, the ALK inhibitor is at a concentration ranging from about 1 µM to about 10 µM. In some embodiments, the first culture medium and/or second culture medium are absent of animal serum.

In some embodiments, the method also comprises isolating the population of hypoimmune dopaminergic neurons from non-dopaminergic neurons. In some embodiments, the method further comprises cryopreserving the isolated population of hypoimmune dopaminergic neurons.

In some aspects, provided herein is an isolated engineered hypoimmune pancreatic islet cell differentiated from a HIPO− cell, wherein endogenous β-2 microglobulin (B2M) gene activity and endogenous class II transactivator (CIITA) gene activity have been eliminated, CD47 expression has been increased, the blood type is O and Rh−.

In some embodiments, the isolated hypoimmune pancreatic islet cell is selected from the group consisting of a pancreatic islet progenitor cell, immature pancreatic islet cell, and mature pancreatic islet cell.

In some aspects, provided herein is a method of treating a patient suffering from diabetes. The method comprises administering a composition comprising a therapeutically effective amount of a population of any one of the isolated hypoimmune pancreatic islet cells described herein. In some embodiments, the composition further comprises a therapeutically effective carrier. In some embodiments, the population of the isolated hypoimmune pancreatic islet cells is on a biodegradable scaffold. In some instances, the administration comprises transplantation or injection.

In some aspects, provided herein is a method of producing a population of hypoimmune pancreatic islet cells from a population of HIPO− cells by in vitro differentiation, wherein endogenous β-2 microglobulin (B2M) gene activity and endogenous class II transactivator (CIITA) gene activity have been eliminated, CD47 expression has been increased, the blood type is O and Rh− in the HIPO− cells. The method comprises: (a) culturing the population of HIPO− cells in a first culture medium comprising one or more factors selected from the group consisting insulin-like growth factor (IGF), transforming growth factor (TGF), fibroblast growth factor (EGF), epidermal growth factor (EGF), hepatocyte growth factor (HGF), sonic hedgehog (SHH), and vascular endothelial growth factor (VEGF), transforming growth factor-β (TGFβ) superfamily, bone morphogenic protein-2 (BMP2), bone morphogenic protein-7 (BMP7), a GSK3β inhibitor, an ALK inhibitor, a BMP type 1 receptor inhibitor, and retinoic acid to produce a population of immature pancreatic islet cells; and (b) culturing the population of immature pancreatic islet cells in a second culture medium that is different than the first culture medium to produce a population of hypoimmune pancreatic islet cells.

In some embodiments, the GSK inhibitor is CHIR-99021, a derivative thereof, or a variant thereof. In some instances, the GSK inhibitor is at a concentration ranging from about 2 µM to about 10 µM. In some embodiments, the ALK inhibitor is SB-431542, a derivative thereof, or a variant thereof. In some instances, the ALK inhibitor is at a concentration ranging from about 1 µM to about 10 µM. In some embodiments, the first culture medium and/or second culture medium are absent of animal serum.

In some embodiments, the method also comprises isolating the population of hypoimmune pancreatic islet cells from non-pancreatic islet cells. In some embodiments, the method further comprises cryopreserving the isolated population of hypoimmune pancreatic islet cells.

In some aspects, provided herein is an isolated, engineered hypoimmune retinal pigmented epithelium (RPE) cell differentiated from a HIPO− cell, wherein endogenous β-2 microglobulin (B2M) gene activity and endogenous class II transactivator (CIITA) gene activity have been eliminated, CD47 expression has been increased, the blood type is O and Rh−.

In some embodiments, the isolated hypoimmune RPE cell is selected from the group consisting of a RPE progenitor cell, immature RPE cell, mature RPE cell, and functional RPE cell.

In some aspects, provided herein is a method of treating a patient suffering from an ocular condition. The method comprises administering a composition comprising a therapeutically effective amount of a population of any one of a population of the isolated hypoimmune RPE cells described herein. In some embodiments, the composition further comprises a therapeutically effective carrier. In some embodiments, the population of the isolated hypoimmune RPE cells is on a biodegradable scaffold. In some embodiments, the administration comprises transplantation or injection to the patient's retina. In some embodiments, the ocular condition is selected from the group consisting of wet macular degeneration, dry macular degeneration, juvenile macular degeneration, Leber's Congenital Ameurosis, retinitis pigmentosa, and retinal detachment.

In some aspects, provided herein is a method of producing a population of hypoimmune retinal pigmented epithelium (RPE) cells from a population of HIPO− cells) by in vitro differentiation, wherein endogenous β-2 microglobulin (B2M) gene activity and endogenous class II transactivator (CIITA) gene activity have been eliminated and CD47 expression has been increased in the HIPO− cells. The method comprises: (a) culturing the population of HIPO− cells in a first culture medium comprising any one of the factors selected from the group consisting of activin A, bFGF, BMP4/7, DKK1, IGF1, noggin, a BMP inhibitor, an ALK inhibitor, a ROCK inhibitor, and a VEGFR inhibitor to produce a population of pre-RPE cells; and (b) culturing the population of pre-RPE cells in a second culture medium that is different than the first culture medium to produce a population of hypoimmune RPE cells.

In some embodiments, the ALK inhibitor is SB-431542, a derivative thereof, or a variant thereof. In some instances, the ALK inhibitor is at a concentration ranging from about 2 µM to about 10 µM. In some embodiments, the ROCK inhibitor is Y-27632, a derivative thereof, or a variant thereof. In some instances, the ROCK inhibitor is at a concentration ranging from about 1 µM to about 10 µM.

In some embodiments, the first culture medium and/or second culture medium are absent of animal serum.

In some embodiments, the method further comprises isolating the population of hypoimmune RPE cells from non-RPE cells. In some embodiments, the method further comprises cryopreserving the isolated population of hypoimmune RPE cells.

In one aspect, human pluripotent stem cells (hiPSCs) are rendered hypo-immunogenic by a) the disruption of the B2M gene at each allele (e.g. B2M−/−), b) the disruption of the CIITA gene at each allele (e.g. CIITA−/−), and c) by the overexpression of the CD47 gene (CD47+, e.g. through introducing one or more additional copies of the CD47 gene or activating the genomic gene). This renders the hiPSC population B2M−/− CIITA−/−CD47tg. In a preferred aspect, the cells are non-immunogenic. In another embodiment, the HIP cells are rendered non-immunogenic B2M−/− CIITA−/−CD47tg as described above but are further modified by including an inducible suicide gene that is induced to kill the cells in vivo when required. In other aspects, HIPO− cells are created when the HIP cells are rendered blood type O by by knocking out the ABO gene Exon 7 or silencing the SLC14A1 (JK) gene and the cells are rendered Rh− by knocking out the C and E antigens of the Rh blood group system (RH), K in the Kell system (KEL), Fya and Fy3 in the Duffy system (FY), Jkb in the Kidd system (JK), or U and S in the MNS blood group system.

F. Maintenance of HIPO− Cells

Once generated, the HIPO− cells can be maintained in an undifferentiated state as is known for maintaining iPSCs. For example, HIP cells are cultured on Matrigel using culture media that prevents differentiation and maintains pluripotency.

G. Differentiation of HIPO− Cells

The invention provides HIPO− cells that are differentiated into different cell types for subsequent transplantation into subjects. As will be appreciated by those in the art, the methods for differentiation depend on the desired cell type using known techniques. The cells are differentiated in suspension and then put into a gel matrix form, such as matrigel, gelatin, or fibrin/thrombin forms to facilitate cell survival. Differentiation is assayed as is known in the art, generally by evaluating the presence of cell-specific markers.

In some embodiments, the HIPO− cells are differentiated into hepatocytes to address loss of the hepatocyte functioning or cirrhosis of the liver. There are a number of techniques that can be used to differentiate HIPO− cells into hepatocytes; see for example Pettinato et al., doi:10.1038/spre32888, Snykers et al., *Methods Mol Biol* 698:305-314 (2011), Si-Tayeb et al. *Hepatology* 51:297-305 (2010) and Asgari et al., *Stem Cell Rev* (493-504 (2013), all of which are hereby expressly incorporated by reference in their entirety and specifically for the methodologies and reagents for differentiation. Differentiation is assayed as is known in the art, generally by evaluating the presence of hepatocyte associated and/or specific markers, including, but not limited to, albumin, alpha fetoprotein, and fibrinogen. Differentiation can also be measured functionally, such as the metabolization of ammonia, LDL storage and uptake, ICG uptake and release and glycogen storage.

In some embodiments, the HIPO− cells are differentiated into beta-like cells or islet organoids for transplantation to address type I diabetes mellitus (T1DM). Cell systems are a promising way to address TDM, see. e.g., Ellis et al., doi/10.1038/nrgastro.2017.93, incorporated herein by reference. Additionally, Pagliuca et al. reports on the successful differentiation of O– cells from hiPSCs (see doi/10.106/j.cell.2014.09.040, hereby incorporated by reference in its entirety and in particular for the methods and reagents outlined there for the large-scale production of functional human β cells from human pluripotent stem cells). Furthermore, Vegas et al. shows the production of human β cells from human pluripotent stem cells followed by encapsulation to avoid immune rejection by the host; (doi:10.1038/nm.4030, hereby incorporated by reference in its entirety and in particular for the methods and reagents outlined there for the large-scale production of functional human β cells from human pluripotent stem cells).

Differentiation is assayed as is known in the art, generally by evaluating the presence of β cell associated or specific markers, including but not limited to, insulin. Differentiation can also be measured functionally, such as measuring glucose metabolism, see generally Muraro et al, doi:10.1016/j.cels.2016.09.002, hereby incorporated by reference in its entirety, and specifically for the biomarkers outlined there.

Once the dHIPO– beta cells are generated, they can be transplanted (either as a cell suspension or within a gel matrix as discussed herein) into the portal vein/liver, the omentum, the gastrointestinal mucosa, the bone marrow, a muscle, or subcutaneous pouches.

In some embodiments, the HIPO– cells are differentiated into retinal pigment epithelium (RPE) to address sight-threatening diseases of the eye. Human pluripotent stem cells have been differentiated into RPE cells using the techniques outlined in Kamao et al., *Stem Cell Reports* 2014:2:205-18, hereby incorporated by reference in its entirety and in particular for the methods and reagents outlined there for the differentiation techniques and reagents; see also Mandai et al., doi:10.1056/NEJMoa1608368, also incorporated in its entirety for techniques for generating sheets of RPE cells and transplantation into patients.

Differentiation can be assayed as is known in the art, generally by evaluating the presence of RPE associated and/or specific markers or by measuring functionally. See for example Kamao et al., doi:10.1016/j.stemcr.2013.12.007, hereby incorporated by reference in its entirety and specifically for the markers outlined in the first paragraph of the results section.

In some embodiments, the HIPO– cells are differentiated into cardiomyocytes to address cardiovascular diseases. Techniques are known in the art for the differentiation of hiPSCs to cardiomyoctes and discussed in the Examples. Differentiation can be assayed as is known in the art, generally by evaluating the presence of cardiomyocyte associated or specific markers or by measuring functionally; see for example Loh et al., doi:10.1016/j.cell.2016.06.001, hereby incorporated by reference in its entirety and specifically for the methods of differentiating stem cells including cardiomyocytes.

In some embodiments, the HIPO– cells are differentiated into endothelial colony forming cells (ECFCs) to form new blood vessels to address peripheral arterial disease. Techniques to differentiate endothelial cells are known. See. e.g., Prasain et al., doi:10.1038/nbt.3048, incorporated by reference in its entirety and specifically for the methods and reagents for the generation of endothelial cells from human pluripotent stem cells, and also for transplantation techniques. Differentiation can be assayed as is known in the art, generally by evaluating the presence of endothelial cell associated or specific markers or by measuring functionally.

In some embodiments, the HIPO– cells are differentiated into thyroid progenitor cells and thyroid follicular organoids that can secrete thyroid hormones to address autoimmune thyroiditis. Techniques to differentiate thyroid cells are known the art. See. e.g. Kurmann et al., doi:10.106/j.stem.2015.09.004, hereby expressly incorporated by reference in its entirety and specifically for the methods and reagents for the generation of thyroid cells from human pluripotent stem cells, and also for transplantation techniques. Differentiation can be assayed as is known in the art, generally by evaluating the presence of thyroid cell associated or specific markers or by measuring functionally.

H. Transplantation of Differentiated HIPO– Cells

As will be appreciated by those in the art, the differentiated HIPO– derivatives are transplated using techniques known in the art that depends on both the cell type and the ultimate use of these cells. In general, the dHIPO– cells of the invention are transplanted either intravenously or by injection at particular locations in the patient. When transplanted at particular locations, the cells may be suspended in a gel matrix to prevent dispersion while they take hold.

In order that the invention described herein may be more fully understood, the following examples are set forth. It should be understood that these examples are for illustrative purposes only and are not to be construed as limiting this invention in any manner.

VIII. EXAMPLES

HIP cells were generated as disclosed in WO2018/132783 and U.S. Prov. App. Nos. 62/698,941, 62/698,965, 62/698,973, 62/698,978, 62/698,981, and 62/698,984, each of which are incorporated by reference herein in their entirety.

A. Example 1: Generation of Human iPSCs

The Human Episomal iPSC Line was derived from CD34+ cord blood (Cat. No. A33124, Termo Fisher Scientific) using a three-plasmid, seven-factor (SOKMNLT; SOX2, OCT4 (POU5F1), KLF4, MYC, NANOG, LIN28, and SV40L T antigen) EBNA-based episomal system from ThermoFisher. This iPSC line is considered to have a zero footprint as there was no integration into the genome from the reprogramming event. It has been shown to be free of all reprogramming genes. The iPSCs have a normal XX karyotype and endogenous expression of pluripotent markers like OCT4, SOX2, NANOG (as shown by RT-PCR) OCT4, SSEA4, TRA-1-60 and TRA-1-81 (as shown by ICC). In directed differentiation and teratoma analyses, these hiPSCs retained their differentiation potential for the ectodermal, endodermal, and mesodermal lineages. In addition, vascular, endothelial, and cardiac lineages were derived with robust efficiencies.

Note:

Several gene-delivery vehicles for iPSC generation were successfully used, including retroviral vectors, adenoviral vectors, Sendai virus as well as virus-free reprogramming methods (using episomal vectors, piggyBac transposon, synthetic mRNAs, microRNAs, recombinant proteins, and small molecule drugs, etc).

Note:

Different factors were successfully used for re-programming, such as the first reported combination of OCT3/4, SOX2, KLF4, and C-MYC, known as the Yamanaka factors. In one embodiment, only three of these factors were successfully combined and omittied C-MYC, although with reduced reprogramming efficiency.

In one embodiment, L-MYC or GLISJ instead of C-MYC showed improved reprogramming efficiency. In another embodiment, reprogramming factors are not limited to genes associated with pluripotency.

a. Statistics

All data are expressed as mean SD or in box blot graphs showing the median and the minimum to maximum range. Intergroup differences were appropriately assessed by either the unpaired Student's t test or the one-way analysis of variance (ANOVA) with Bonferroni's postHoc test. * $p<0.05$, ** $p<0.01$.

B. Example 2: Generation of Human HIP Cells

Human Cas9 iPSC underwent 2 gene-editing steps. In the first step, CRISPR technology was performed by a combined targeting of the coding sequence of human beta-2-microglobuline (B2M) gene with the CRISPR sequence 5'-CGTGAGTAAACCTGAATCTT-3' (SEQ ID NO: 7) and the coding sequence of human CIITA gene with the CRISPR sequence 5'-GATATGGCATAAGCCTCCC-3' (SEQ ID NO: 8). Linearized CRISPR sequence with T7 promoter was used to synthesize gRNA as per the kit's instructions (MEGAshortscript T7 Transcription Kit, Thermo Fisher). The collected in-vitro transcription (IVT) gRNA was then purified via the MEGAclear Transcription Clean-Up Kit. For IVT gRNA delivery, singularized cells were electroporated with 300ng IVT gRNA using a Neon electroporation system. After electroporation, edited Cas9 iPSCs were expanded for single cell seeding: iPSC cultures were dissociated to single cells using TrypLE (Gibco) and stained with Tral-60 Alexa Fluor® 488 and propidium iodide (PI). FACS Aria cell sorter (BD Biosciences) was used for the sorting and doublets and debris were excluded from seeding by selective gating on forward and side scatter emission. Viable pluripotent cells were selected on the absence of PI and presence of Tral-60 Alexa Fluor 488 staining. Single cells were then expanded into full size colonies, after which the colonies were tested for a CRISPR edit. CRISPR mediated cleavage was assessed using the GeneArt Genomic Cleavage Detection Kit (Thermo Fisher). Genomic DNA was isolated from $1\times10^6$ hiPSCs and the B2M and CIITA genomic DNA regions were PCR amplified using AmpliTaq Gold 360 Master Mix and the primer sets F: 5'-TGGGGCCAAAT-CATGTAGACTC-3' (SEQ ID NO: 9) and R: 5'-TCAGTGGGGGTGAATCAGTGT-3' (SEQ ID NO: 10) for B2M as well as F: 5'-CTAACAGCGATGCTGACCCC-3' (SEQ ID NO: 11) and R: 5'-TGGCCTC-CATCTCCCCTCTCT-3' (SEQ ID NO: 12) for CIITA. For TIDE analysis, the obtained PCR product was cleaned up (PureLink PCR Purification Kit, Thermo Fisher) and Sanger sequencing was performed for the prediction of indel frequency. After the confirmation of B2M/CIITA knockout, cells were further characterized through karyotype analysis and the TaqMan hPSC Scorecard Panel (Thermo Fisher). The PSC were found to be pluripotent and maintained a normal (46, XX) karyotype during the genome editing process.

In the second step, the CD47 gene was synthesized and the DNA was cloned into a plasmid lentivirus with an EF1a promotor and puromycin resistance. Cells were transduced with lentiviral stocks of $1\times10^7$ TU/mL and 6 µg/mL of Polybrene (Thermo Fisher). Media was changed daily after transduction. Three days after transduction, cells were expanded and selected with 0.5 µg/mL of puromycin. After 5 days of antibiotic selection, antibiotic resistant colonies emerged and were further expanded to generate stable pools. Level of CD47 was confirmed by qPCR. Pluripotency assay (TaqMan hPSC Scorecard Panel, Thermo Fisher). and karyotyping were performed again to verify the pluripotent status of the cells.

C. Example 3: HIP Cell Rejection in Rhesus Macaque Monkeys and Pigs 10 million hypo-iPSC derived endothelial cells (expressing luciferase) were injected subcutaneously into rhesus macaque monkeys and cells were longitudinally followed using bioluminescence imaging; each animal was injected intravenously with 100 mg/ml D-luciferin (PerkinElmer, San Jose, Calif.) via a peripheral vessel for in vivo imaging using a Xenogen IVIS®200 Series imaging system (Caliper Life Sciences, Alameda, Calif., Cat. No. 122799). Our pre-transplant screening assays and validation studies predicted that the cells would not be rejected, resulting in stable BLI signals. The BLI-signals decreased, however, on day 6 and were not detected by day 16. In addition, "bumps" were observed on the injection sites (data not shown). Blood was drawn from the same monkeys and T cell, cytotoxic T cell, NK cell (FIG. 1A), B cell (DSA; donor specific antibodies), or macrophages activation (FIG. 1B) was not observed. Blood typing the monkeys by PCR confirmed that all tested monkeys were blood type B. Therefore, the hypo-immunogenic endothelial cell transplantation was ABO mismatched (data not shown).

D. Example 4: IgM Antibodies Killed Endothelial Cells from hiPSCs

Blood type rejection was confirmed by incubating human hypo-immunogenic endothelial cells with rhesus macaque serum.

Human iPSC Differentiation into hiECs. hiPSC were plated on diluted Matrigel (Corning, Tewksbury, Mass., Cat. No. 356231) in six-well plates and maintained in Essential 8 Flex media (Thermo Fisher, Cat. No. A2858501). The differentiation was started at 60% confluency and media was changed to RPMI-1640 containing 2% B-27 minus insulin (both Gibco Thermo Fisher, Cat. No. A1895601) and 5 µM CHIR-99021 (Selleckchem, Cat. No. S1263). On day 2, the media was changed to reduced media: RPMI-1640 containing 2% B-27 minus insulin and 2 µM CHIR-99021. From day 4 to 7, cells were exposed to RPMI-1640 EC media (RPMI-1640, 2% B-27 minus insulin, 50 ng ml/human vascular endothelial growth factor (VEGF, Peprotech, Rocky Hill, N.J., Cat. No. 100-20), 10 ng ml-1 human fibroblast growth factor basic (FGFb; Peprotech, Cat. No. 100-18B), 10 µM Y-27632 (Selleckchem, Cat. No. S1049), and 1 µM SB 431542 (Reagentsdirect, Cat. No. 21-A94).

Endothelial cell clusters were visible from day 7 and cells were maintained in EGM-2 SingleQuots media (Lonza, Basel, Switzerland, Cat. No. CC-3162) plus 10% Fetal Calf Serum hi (Gibco Thermo Fisher, Cat. No. 10082147), 25 ng ml-1 VEGF, 2 ng ml-1 FGFb, 10 µM Y-27632 and 1 µM SB 431542. The differentiation process was completed after 14 days and undifferentiated cells detached during the differentiation process. For purification, cells were treated with 20 µM PluriSln-1 (StemCell Technologies, Cambridge, Mass., Cat. No. 72824) for 48 hours. The highly purified ECs were cultured in EGM-2 SingleQuots media plus supplements and 10% FCS hi (Gibco). TrypLE Express was used for passaging the cells 1:3 every 3-4 days.

When human hypo-immunogenic endothelial cells (blood type A) were incubated with rhesus macaque serum (blood type B), cells were killed immediately. The antibody type that killed the cells was determined by antibody depletion analyses.

IgM depletion was done in a working solution of 50 mM dithiothreitol (DTT, Millipore Sigma, St. Louis, Mo., Cat. No. D0632). 10 µl of DTT were mixed with 90 µl serum.

IgG depletion was done with Pierce Protein Beads (Thermo Fisher, Waltham, Mass., Cat. No. 88803). The beads were washed in the wash buffer and collected magnetically. 0.5 mg of the washed beads were combined with 100 µl of the rhesus macaque serum and incubated for 60 minutes at room temperature with gentle inversion every 10 minutes. The beads were separated magnetically, the serum was transferred to a new tube and kept on ice until used.

Depletion of either IgM or IgG antibodies demonstrated that the ABO– antibodies are from the IgM type (FIG. 2). Blood type rejection was also similarly confirmed by IgM and IgG depletion using HIP-derived cardiomyocites and adult cardiac tissue (Celprogen, Torrance, Calif., Cat. No. 36044-15-T75, data not shown)).

E. Example 5: Human HIP or iPSC Differentiated into Cardiac Myocytes Survive Blood Group Matched Xenogeneic Exposure The human cells were not rejected by other pre-formed antibodies when transplanted across the xenogeneic barrier. Human HIP-derived endothelial cells (blood type A) were rejected when incubated with ABO– mismatched rhesus macaque serum (blood type B). When serum from rhesus macaque with blood type AB was used, however, the human cells survived (FIG. 3). Thus, rhesus macaques do not have other pre-existing antibodies against human cells.

Human iPSC were differentiated into hiCMs. hiPSCs were plated on diluted Matrigel in six-well plates and maintained in Essential 8 Flex media (Thermo Fisher). Differentiation was started at 90% confluency, and media was changed to 5 ml of RPMI-1640 containing 2% B-27 minus Insulin and 6 µM CHIR-99021. After 2 days, media was changed to RPMI-1640 containing 2% B-27 minus insulin without CHIR. On day 3, 5 µl IWR1 (Selleckchem, Houston, Tex., Cat. No. S7086) was added to the media for two further days. At day 5, the media was changed back to RPMI-1640 containing 2% B-27 minus insulin medium and left for 48 h. At day 7, media was changed to RPMI-1640 containing B27 plus insulin and replaced every 3 days thereafter with the same media. Spontaneous beating of cardiomyocytes was first visible around day 10. Purification of cardiomyocytes was performed on day 10 post-differentiation. Briefly, media was changed to low glucose media and maintained for 3 days. At day 13, media was changed back to RPMI-1640 containing B27 plus insulin. This procedure was repeated on day 14.

The human hypo-immunogenic iPSC-derived endothelial cells (blood type A) survive when incubated with allogeneic human serum blood type A and AB. However, serum containing pre-formed antibodies against A (blood type O and B) killed the cells immediately (FIG. 4).

Translational analyses were performed by incubating pig serum (blood type A) with human endothelial cells from all blood types. Only those cells with blood type B or AB were killed (data not shown). This confirms that human cells are hyperacutely rejected when transplanted into ABO mismatched pigs.

F. Example 6: Generation of Human HIPO– Cells

In some aspects, HIPO– cells are generated using blood type O Rh– pluripotent stem cells as starter cells and following the HIP cell generation protocols described herein. Therefore, the HIP cells are HIPO– cells.

In other aspects, a HIPO– cell is generated from a non-universal blood group iPSC, ESC or HIP cell. For example, a blood type B– embryonic or iPSC cell line is transformed into O– by generating a knock-out cell line in the ABO gene using CRISPR technology for targeting of the coding sequence (gene ID: 28; Ensembl: ENSG00000175164 MIM:110300). Therefore, CRISPR guide RNAs targeting the coding sequence of the B gene are ligated into vectors containing the Cas9 expression cassette and subsequently transfected into hiPSCs. Linearized CRISPR sequence with T7 promoter are used to synthesize gRNA as per the kit's instructions (MEGAshortscript T7 Transcription Kit, Thermo Fisher). The resulting in vitro transcription (IVT) gRNA is then purified via the MEGA-clear Transcription Clean-Up Kit. For IVT gRNA delivery, cells are electroporated with 300 ng IVT gRNA using a Neon electroporation system using 1,200 V, 30 ms, 1 pulse into hiPSC stably expressing Cas9.

After electroporation, edited hiPSC are expanded for single cell seeding: hiPSC cultures are dissociated into single cells using TrypLE Express (Gibco) and stained with Alexa Fluor 488-conjugated anti-TRA-160 mAb and propidium iodide. A FACSAria II cell sorter (BD Biosciences) is used for the sorting and doublets and debris are excluded from seeding by selective gating on forward and side light scatter properties. Viable pluripotent cells are selected on the absence of propidium iodide and presence of Tral-60 staining. Single cells are then expanded into full-size colonies, after which the colonies are tested for CRISPR editing by sequencing.

CRISPR-mediated cleavage is assessed using the GeneArt Genomic Cleavage Detection Kit (Ihermo Fisher) for testing of the initial edited pools. For screening the isolated clones, genomic DNA is isolated from $1 \times 10^6$ hiPSCs and the B genomic DNA regions are PCR amplified using AmpliTaq Gold 360 Master Mix. For TIDE analysis, the resulting PCR product is cleaned up (PureLink PCR Purification Kit, Thermo Fisher) and Sanger sequencing is performed for the prediction of indel frequency. After the confirmation of B disruption, cells are further characterized through karyotype analysis and the TaqMan hiPSC Scorecard Panel (Thermo Fisher).

Another example is using a O rh+ cell line and transforming this into a O rh-cell line by deleting RHAG (Rh-associated glycoprotein; ammonium transport; associated with RhD; chromosome 6p21-qter) using CRISP/Cas9 technology as described above (RHAG gRNA sequence: CCAGTGGGGCACTATTGTAC (SEQ ID NO: 13)).

G. Example 7: Differentiation of Human HIPO– Cells

1. Differentiation of hHIPO– Cells to Human Cardiomyocytes

This is done using a protocol adapted from Sharma et al. J. Vis Exp. 2015 doi: 10.3791/52628, hereby incorporated by reference in its entirety and specifically for the techniques to differentiate the cells. HIPO– cells are plated on diluted Matrigel (356231, Corning) in 6-well plates and maintained in Essential 8 Flex media (Thermo Fisher). After the cells arrive at 90% confluency, the differentiation is started and media is changed to 5 mL of RPMI1640 containing 2% B-27 minus Insulin (both Gibco) and 6 uM CHIR-99021 (Selleck Chem). After 2 days, media is changed to RPMI1640 containing 2% B-27 minus Insulin without CHIR. On day 3, 5 uL IWR1 is added to the media for two further days. At day 5, the media is changed back to RPMI 1640 containing 2% B-27 minus insulin medium and incubated for 48 hr. At day 7, media is changed to RPMI 1640 containing B27 plus insulin (Gibco) and replaced every 3 days thereafter with the same media. Spontaneous beating of cardiomyocytes may first be visible at approximately day 10 to day 12. Purification of Cardiomyocytes is performed on day 10 post-differentiation. Briefly, media is changed to low glucose media and maintained for 3 days. At day 13, media is changed back to RPMI 1640 containing B27 plus insulin. This procedure is repeated on day 14. The remaining cells are highly purified cardiomyocytes.

2. Differentiation of HIPO– Cells to Human Endothelial Cells

HIPO– cells are plated on diluted Matrigel (356231, Corning) in 6-well plates and maintained in Essential 8 Flex media (Thermo Fisher). After the cells arrive at 60% confluency, the differentiation is started and media is changed to RPMI1640 containing 2% B-27 minus Insulin (both Gibco) and 5 μM CHIR-99021 (Selleck Chem). On day 2, the media is changed to reduced media: RPMI1640 containing 2% B-27 minus Insulin (both Gibco) and 2 μM CHIR-99021 (Selleck Chem). From day 4 to day 7, cells are exposed to RPMI EC media, RPMI1640 containing 2% B-27 minus Insulin plus 50 ng/mL vascular endothelial growth factor (VEGF; R&D Systems, Minneapolis, Minn., USA), 10 ng/mL fibroblast growth factor basic (FGFb; R&D Systems), 10 μM Y-27632 (Sigma-Aldrich, Saint Louis, Mo., USA) and 1 μM SB 431542 (Sigma-Aldrich). Endothelial cell clusters are visible from day 7 and cells are maintained in EGM-2 SingleQuots media (Lonza, Basel, Switzerland) plus 10% FCS hi (Gibco), 25 ng/mL vascular endothelial growth factor (VEGF; R&D Systems, Minneapolis, Minn., USA), 2 ng/mL fibroblast growth factor basic (FGFb; R&D Systems), 10 μM Y-27632 (Sigma-Aldrich, Saint Louis, Mo., USA) and 1 μM SB 431542 (Sigma-Aldrich). The differentiation process may be completed after 14 days und undifferentiated cells detach during the differentiation process. For purification, cells go through MACS progress according to the manufactures' protocol using CD31 microbeads (Miltenyi, Auburn, Calif.). The highly purified EC-cells are cultured in EGM-2 SingleQuots media (Lonza, Basel, Switzerland) plus supplements and 10% FCS hi (Gibco). TrypLE was used for passaging the cells 1:3 every 3 to 4 days.

IX. EXEMPLARY SEQUENCES

Human β-2-Microglobulin
SEQ ID NO: 1
MSRSVALAVLALLSLSGLEAIQRTPKIQVYSRHPAENGKSNFLNCYVSGF

HPSDIEVDLLKNGERIEKVEHSDLSFSKDWSFYLLYYTEFTPTEKDEYAC

RVNHVTLSQPKIVKWDRDI

Human CIITA protein, 160 amino acid N-terminus
SEQ ID NO: 2
MRCLAPRPAGSYLSEPQGSSQCATMELGPLEGGYLELLNSDADPLCLYHF

YDQMDLAGEEEIELYSEPDTDTINCDQFSRLLCDMEGDEETREAYANIAE

LDQYVFQDSQLEGLSKDIFKHIGPDEVIGESMEMPAEVGQKSQKRPFPEE

LPADLKHWKP

Human CD47
SEQ ID NO: 3
MWPLVAALLLGSACCGSAQLLFNKTKSVEFTFCNDTVVIPCFVTNMEAQN

TTEVYVKWKFKGRDIYTFDGALNKSTVPTDFSSAKIEVSQLLKGDASLKM

DKSDAVSHTGNYTCEVTELTREGETIIELKYRVVSWFSPNENILIVIFPI

FAILLFWGQFGIKTLKYRSGGMDEKTIALLVAGLVITVIVIVGAILFVPG

EYSLKNATGLGLIVTSTGILILLHYYVFSTAIGLTSFVIAILVIQVIAYI

LAVVGLSLCIAACIPMHGPLLISGLSILALAQLLGLVYMKFVE

Herpes Simplex Virus Thimidine Kinase (HSV-tk)
SEQ ID NO: 4
MASYPCHQHASAFDQAARSRGHSNRRTALRPRRQQEATEVRLEQKMPTLL

RVYIDGPHGMGKTTTTQLLVALGSRDDIVYVPEPMTYWQVLGASETIANI

YTTQHRLDQGEISAGDAAVVMTSAQITMGMPYAVTDAVLAPHVGGEAGSS

HAPPPALTLIFDRHPIAALLCYPAARYLMGSMTPQAVLAFVALIPPTLPG

TNIVLGALPEDRHIDRLAKRQRPGERLDLAMLAAIRRVYGLLANTVRYLQ

GGGSWWEDWGQLSGTAVPPQGAEPQSNAGPRPHIGDTLFTLFRAPELLAP

NGDLYNVFAWALDVLAKRLRPMHVFILDYDQSPAGCRDALLQLTSGMVQT

HVTTPGSIPTICDLARTFAREMGEAN

Escherichia coli Cytosine Deaminase (EC-CD)
SEQ ID NO: 5
MSNNALQTIINARLPGEEGLWQIHLQDGKISAIDAQSGVMPITENSLDAE

QGLVIPPFVEPHIHLDTTQTAGQPNWNQSGTLFEGIERWAERKALLTHDD

VKQRAWQTLKWQIANGIQHVRTHVDVSDATLTALKAMLEVKQEVAPWIDL

QIVAFPQEGILSYPNGEALLEEALRLGADVVGAIPHFEFTREYGVESLHK

TFALAQKYDRLIDVHCDEIDDEQSRFVETVAALAHHEGMGARVTASHTTA

MHSYNGAYTSRLFRLLKMSGINFVANPLVNIHLQGRFDTYPKRRGITRVK

EMLESGINVCFGHDDVFDPWYPLGTANMLQVLHMGLHVCQLMGYGQINDG

LNLITHHSARTLNLQDYGIAAGNSANLIILPAENGFDALRRQVPVRYSVR

GGKVIASTQPAQTTVYLEQPEAIDYKR

Truncated human Caspase 9
SEQ ID NO: 6
GFGDVGALESLRGNADLAYILSMEPCGHCLIINNVNFCRESGLRTRTGSN

IDCEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLFFI

QACGGEQKDHGFEVASTSPEDESPGSNPEPDATPFQEGLRTFDQLDAISS

LPTPSDIFVSYSTFPGFVSWRDPKSGSWYVETLDDIFEQWAHSEDLQSLL

LRVANAVSVKGIYKQMPGCFNFLRKKLFFKTS

All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

What is claimed:

1. An ABO blood group type O (O) and a Rhesus Factor (Rh) blood type negative (−) induced pluripotent cell, comprising,
   a. an endogenous Major Histocompatibility Antigen Class I (HLA-I) function that is reduced when compared to a parent pluripotent cell;
   b. an endogenous Major Histocompatibility Antigen Class II (HLA-II) function that is reduced when compared to said parent pluripotent cell; and
   c. an increased expression of CD47 when compared to said parental pluripotent cell;
wherein the increased expression of CD47 is caused by a transgene encoding CD47 operably linked to a constitutive promoter, and wherein said increased CD47 expression causes a reduced susceptibility to NK cell or macrophage killing when compared to said parent pluripotent cell.

2. The induced pluripotent cell of claim 1, wherein said ABO blood group type O results from reduced ABO blood group protein expression.

3. The induced pluripotent cell of claim 1, wherein said ABO blood group is endogenously type O.

4. The induced pluripotent cell of claim 1, wherein said ABO blood group type O results from a disruption in human Exon 7 of the ABO gene.

5. The induced pluripotent cell of claim 1, wherein said Rh blood group is endogenously type Rh−.

6. The induced pluripotent cell of claim 1, wherein said Rh blood group results from a reduced Rh protein expression.

7. The induced pluripotent cell of claim 1, wherein said type Rh− results from a disruption in an Rh C antigen, an Rh E antigen, a Kell K antigen (KEL), a Duffy (FY) Fya antigen, a Duffy Fy3 antigen, a Kidd (JK) Jkb antigen, or a Kidd SLC14A1 gene.

8. The induced pluripotent cell of claim 1, wherein said HLA-I function is reduced by a knock out of β-2 microglobulin, HLA-A, HLA-B, or HLA-C genes.

9. The induced pluripotent cell of claim 1, wherein said HLA-II function is reduced by a knock out in class II transactivator (CIITA), or HLA-DP, HLA-DR, or HLA-DQ genes.

10. The induced pluripotent cell of claim 1, further comprising a suicide gene that is activated by a trigger that causes said pluripotent cell to die.

11. The pluripotent cell of claim 10, wherein said suicide gene is selected from the group consisting of:
    a. a herpes simplex virus thymidine kinase gene (HSV-tk) and said trigger is ganciclovir
    b. an *Escherichia coli* cytosine deaminase gene (EC-CD) and said trigger is 5-fluorocytosine (5-FC), and
    c. an inducible Caspase protein and said trigger is a chemical inducer of dimerization (CID).

12. An ABO blood group type O (O) and a Rhesus Factor (Rh) blood type negative embryonic stem cell, comprising,
    a. an endogenous Major Histocompatibility Antigen Class I (HLA-I) function that is reduced when compared to a parent embryonic stem cell;
    b. an endogenous Major Histocompatibility Antigen Class II (HLA-II) function that is reduced when compared to said parent embryonic stem cell;
    c. an increased expression of CD47 when compared to said parent embryonic stem cell;
wherein the increased expression of CD47 is caused by a transgene encoding CD47 operably linked to a constitutive promoter, and wherein said increased CD47 expression causes a reduced susceptibility to NK cell or macrophage killing when compared to said parent embryonic stem cell.

13. The modified embryonic stem cell of claim 12, wherein said ABO blood group type O results from reduced ABO blood group protein expression.

14. The modified embryonic stem cell of claim 12, wherein said ABO blood group is endogenously type O.

15. The modified embryonic stem cell of claim 12, wherein said ABO blood group type O results from a disruption in human Exon 7 of the ABO gene.

16. The modified embryonic stem cell of claim 12, wherein said Rh blood group is endogenously type Rh−.

17. The modified embryonic stem cell of claim 12, wherein said Rh blood group results from a reduced Rh protein expression.

18. The modified embryonic stem cell of claim 12, wherein said type Rh− results from a disruption in an Rh C antigen, an Rh E antigen, a Kell K antigen (KEL), a Duffy (FY) Fya antigen, a Duffy Fy3 antigen, a Kidd (JK) Jkb antigen, or a Kidd SLC14A1 gene.

19. The modified embryonic stem cell of claim 12, wherein said HLA-I function is reduced by a knock out of β-2 microglobulin, HLA-A, HLA-B, or HLA-C genes.

20. The modified embryonic stem cell of claim 12, wherein said HLA-II function is reduced by a knock out in class II transactivator (CIITA), or HLA-DP, HLA-DR, or HLA-DQ genes.

21. The modified embryonic stem cell of claim 12, further comprising a suicide gene that is activated by a trigger that causes said hypoimmunogenic pluripotent cell to die.

22. The modified embryonic stem cell of claim 12, wherein said suicide gene is selected from the group consisting of:
    a. a herpes simplex virus thymidine kinase gene (HSV-tk) and said trigger is ganciclovir
    b. an *Escherichia coli* cytosine deaminase gene (EC-CD) and said trigger is 5-fluorocytosine (5-FC); and
    c. an inducible Caspase protein and said trigger is a chemical inducer of dimerization (CID).

* * * * *